(12) United States Patent
Randolph et al.

(10) Patent No.: US 6,864,301 B2
(45) Date of Patent: *Mar. 8, 2005

(54) PREPARATION AND USE OF PHOTOPOLYMERIZED MICROPARTICLES

(75) Inventors: Theodore Randolph, Niwot, CO (US);
Kristi Anseth, Boulder, CO (US);
Jennifer L. Owens, Boulder, CO (US);
Corinne Lengsfeld, Denver, CO (US)

(73) Assignee: The Regents of the University of Colorado, Boulder, CO (US)

( * ) Notice: Subject to any disclaimer, the term of this patent is extended or adjusted under 35 U.S.C. 154(b) by 216 days.

This patent is subject to a terminal disclaimer.

(21) Appl. No.: 10/161,544

(22) Filed: Jun. 3, 2002

(65) Prior Publication Data

US 2003/0045597 A1 Mar. 6, 2003

Related U.S. Application Data

(63) Continuation-in-part of application No. 09/451,481, filed on Nov. 30, 1999, now Pat. No. 6,403,672.
(60) Provisional application No. 60/110,816, filed on Nov. 30, 1998.

(51) Int. Cl.[7] .............................. C08J 3/28; C08J 9/00; C08K 5/00

(52) U.S. Cl. .............................. 522/74; 522/75; 522/78; 522/79; 522/80; 522/82; 521/50.5; 524/104; 524/205; 524/280; 524/361; 524/379

(58) Field of Search .............................. 522/74, 75, 78, 522/79, 80, 82, 179, 182, 183; 521/50.5; 524/104, 205, 280, 361, 379; 427/2.14, 2.21; 527/200–315

(56) References Cited

U.S. PATENT DOCUMENTS 5,496,901 A 3/1996 DeSimone (List continued on next page.)

FOREIGN PATENT DOCUMENTS

EP 0 464 163 B1 4/1995

OTHER PUBLICATIONS

Bodmeier, R. et al. (1995), "Polymeric Microspheres Prepared by Spraying into Compressed Carbon Dioxide," Pharm. Res. 12(8):1211–1217.

(List continued on next page.)

*Primary Examiner*—Susan Berman
(74) *Attorney, Agent, or Firm*—Greenlee, Winner and Sullivan, P.C.

(57) ABSTRACT

Methods of forming crosslinked polymer particles in situ from polymer precursors such as monomers or oligomers, comprising exposing a composition comprising at least one polymer precursor, a solvent or solvent mixture, and an antisolvent or antisolvent mixture to photoradiation under conditions whereby particles are formed are provided. The polymer precursor may be photosensitive, or a separate polymerization initiator may be used. In a preferred embodiment, the polymer precursor is insoluble in the antisolvent or antisolvent mixture and the solvent or solvent mixture is soluble in the antisolvent or antisolvent mixture at the concentrations used. Crosslinked polymer particles and crosslinked polymer particles comprising a polymer and a bioactive material are also provided. The polymer may be erodable, and the polymer particles formed may be used in a variety of applications, including controlled release of bioactive materials such as drugs. Polymer particles formed using the methods of the invention have low residual solvent levels and high additive encapsulation efficiencies. The processes of the invention allow control of particle size and morphology, use low operating temperatures and are useful for efficient bulk production.

11 Claims, 17 Drawing Sheets

U.S. PATENT DOCUMENTS

| | | | |
|---|---|---|---|
| 5,552,502 A | 9/1996 | Odell et al. | |
| 5,603,960 A | 2/1997 | O'Hagen et al. | |
| 5,626,863 A | 5/1997 | Hubbell et al. | |
| 5,639,441 A | 6/1997 | Sievers et al. | 424/9.3 |
| 5,707,634 A | 1/1998 | Schmitt | 424/400 |
| 5,770,559 A | 6/1998 | Manning et al. | 514/2 |
| 5,814,678 A | 9/1998 | Randolph | 522/18 |
| 5,833,891 A | 11/1998 | Subramanian et al. | 264/7 |
| 5,837,752 A | 11/1998 | Shastri et al. | |
| 5,874,029 A | 2/1999 | Subramaniam et al. | 264/12 |
| 5,902,599 A | 5/1999 | Anseth et al. | |
| 5,981,474 A | 11/1999 | Manning et al. | 514/2 |
| 6,063,138 A | 5/2000 | Hanna et al. | |
| 6,143,211 A | 11/2000 | Mathiowitz et al. | |

OTHER PUBLICATIONS

Cooper, A.I. and Holmes, A.B. (1998), "Surfactant–Free Synthesis of Cross–Linked Polymer Microspheres," Proc. 5$^{th}$ Meeting of Supercritical Fluids Materials and Natural Products Processing, held Mar. 23–25, 1998, France, pp. 843–848.

Debenedetti, P.G. et al. (1993), "Supercritical Fluids: A New Medium for the Formation of Particles of Biomedical Interest," Proceedings Internatl. Symp. Control Rel. Bioact. Mater. 20, Controlled Release Society, Inc., pp. 141–142.

Debenedetti, P.G. et al. (1993), "Application of supercritical fluids for the production of sustained delivery devices," J. Controlled Release 24:27–44.

Debenedetti, P.G. et al. (1993), "Rapid Expansion of Supercritical Solutions (RESS): Fundamentals and Applications," Fluid Phase Equilibria 82:311–321.

Dixon, D.J. and Johnston, K.P. (1993), "Formation of Microporous Polymer Fibers and Oriented Fibrils by Precipitation with a Compressed Fluid Antisolvent," J. Appl. Polym. Sci. 50:1929–1942.

Falk and Randolph (Aug. 1998), "Process Variable Implications for Residual Solvent Removal and Polymer Morphology in the Formation of Gentamycin–Loaded Poly (L–lactide) Microparticles," Pharm. Res. 15(8):1233–1237.

Kloosterboer, J. (1988), "Network Formation by Chain Crosslinking Photopolymerization and its Applications in Electronics," J. Adv. Poly. Sci. 84:1–61.

Langer, R. (1993), "Polymer–Controlled Drug Delivery Systems," Acc. Chem. Res. 26:537–542.

Lovell, L.G. et al. (Jun. 2001), "Understanding the Kinetics and Network Formation of Dimethacrylate Dental Resins," Polym. Adv. Technol.12:335–345.

Lu and Anseth (Apr. 2000), "Release Behavior of High Molecular Weight Solutes from Poly(ethylene glycol)–Based Degradable Networks," Macromolecules, pp. 2509–2515.

Muggli, D.S. et al. (Jun. 1998), "Reaction Behavior of Biodegradable, Photo–Cross–Linkable Polyanhydrides," Macromolecules 31:4120–4125.

Muggli, D.S. et al. (Aug. 1999), "Crosslinked Polyanhydrides for Use in Orthopedic Applications: Degradation Behavior and Mechanics," J. Biomed. Mater. Res. 46:271–278.

Oh, J.S. et al. (Apr. 1999), "Swelling behavior of N–isopropylacrylamide gel particles with degradable crosslinker," Eur. Polym. J. 35(4):621–630 (Abstract Only).

Randolph, T.W. et al. (1993), "Sub–Micrometer–Sized Biodegradable Particles of Poly(L–Lactic Acid) via the Gas Antisolvent Spray Precipitation Process," Biotechnol. Prog. 9:429–435.

Tom, J.W. et al. (1993), "Applications of Supercritical Fluids in the Controlled Release of Drugs," in *Supercritical Fluid Engineering Science*, pp. 238–257.

Tom, J.W. and Debenedetti, P.G. (1991), "Formation of Bioerodible Polymeric Microspheres and Microparticles by Rapid Expansion of Supercritical Solutions," Biotechnol. Prog. 7:403–411.

Yeo, S.–D. et al. (1993), "Formation of Microparticulate Protein Powders Using a Supercritical Fluid Antisolvent," Biotechnol. Bioeng. 41:341–346.

PREPARATION AND USE OF PHOTOPOLYMERIZED MICROPARTICLES

CROSS-REFERENCE TO RELATED APPLICATIONS

This application takes priority from U.S. provisional Patent Application No. 60/110,816, filed Nov. 30, 1998, and is a continuation in part of U. S. patent application Ser. No. 09/451,481, filed Nov. 30, 1999, now U.S. Pat. No. 6,403, 672, which are hereby incorporated in their entirety by reference to the extent not inconsistent with the disclosure herein.

STATEMENT REGARDING FEDERALLY SPONSORED RESEARCH OR DEVELOPMENT

This invention was made with government support by the National Institutes of Health under grant number 5 R01 HL59400 and the National Science Foundation. The federal government may have certain rights in this invention.

BACKGROUND OF THE INVENTION

This invention relates generally to polymer particles and methods of making and using the same.

Small (micron- and nano-sized) polymer particles are useful for many applications, including pharmaceutical uses. Polymer microparticles are useful for injectable and implantable devices because they have a long circulation time in the body and are efficient drug, enzyme, and protein carriers (Tom, J. W. et al. (1993), "Applications of Supercritical Fluids in the Controlled Release of Drugs," in *Supercritical Fluid Engineering Science*, pp. 238–257). Crosslinked polymer microparticles have material property benefits over linear polymer particles including improved mechanical strength, greater control of transport properties, material property adjustability and dimensional stability. Some applications of crosslinked polymers are listed in Cooper, A. L. and Holmes, A. B. (1998) Proceedings of the 5th Meeting of Supercritical Fluids Materials and Natural Products Processing, pp. 843–848. Polymer microparticles (both linear and crosslinked) have been used in applications such as dental composites, biostructural fillers and controlled release devices. Some applications of synthetic bone composites are listed in Popov, V. K. et al. (1998) Proceedings of the 5th Meeting of Supercritical Fluids Materials and Natural Products Processing, pp. 45–50.

Controlled release devices are useful in many applications, from medical to agricultural purposes. (Langer, R. (1993), Polymer-Controlled Drug Delivery Systems," Acc. Chem. Res. 26:537–542; U.S. Pat. No. 5,043,280). Controlled release delivery systems for drugs have a wide variety of advantages over conventional forms of drug administration. Some of these advantages include: decreasing or eliminating the oscillating drug concentrations found with multiple drug administrations; allowing the possibility of localized delivery of the drug to a desired part of the body; preserving the efficacy of fragile drugs; reducing the need for patient follow-up care; increasing patient comfort; and improving patient compliance. (Langer, R. (1990), "New Methods of Drug Delivery," Science 249:1527–1533).

Crosslinked polymeric release devices have the capability to modify the release profile of a drug or other chemical by modifying the structure of the crosslinked polymer network. A crosslinked polymer network can provide diffusion controlled release of a drug or other chemical. The rate of diffusion of the drug or other bioactive material to be released can be influenced by the mesh size of the network, or the distance between crosslinks, which depends upon the extent of crosslinking in the network. In a biodegradable system, the mesh size of the network will increase with time as the network degrades.

Current polymer microparticle manufacturing techniques all suffer from one or more disadvantages. For example, the spray drying technique usually requires evaporation of solvent in hot air. The high temperatures used can degrade sensitive drugs and polymers. In thermal polymerization, monomer is heated to induce polymerization. Again, the high temperatures used can cause degradation (including lowering the activity of biologically active substances).

Emulsion and suspension polymerizations (see, for example, U.S. Pat. No. 5,603,960 (O'Hagan., et al.)) involve combinations of solvents, emulsifiers, and surfactants where dispersed islands of monomer polymerize through chemical reaction in a sea of solvent. These methods often involve operation at high temperatures and thus have the problems discussed above, use large volumes of solutions that are often environmentally unfriendly, and permit only minimal control over particle size and morphology.

A number of different techniques have been developed to form small particles of polymers using the solvent power of supercritical fluids. Supercritical fluids have liquid-like densities, very large compressibilities, viscosities between those of liquids and gases, and diffusion coefficients that are higher than liquids. Due to the high compressibility, the density (and solvent power) of a supercritical fluid can be adjusted between gas- and liquid-like extremes with moderate changes in pressure (Debenedetti, P. G. et al. (1993), "Rapid Expansion of Supercritical Solutions (RESS): Fundamentals and Applications," Fluid Phase Equilibria 82:311–321).

The Rapid Expansion of Supercritical Solution (RESS) technique has been used to form small particles of poly(L-lactic acid) (Debenedetti, P. G. et al. (1993), "Supercritical Fluids: A New Medium for the Formation of Particles of Biomedical Interest," Proceed. Intern. Symp. Control Rel. Bioact. Mater. 20:141–142) and particles of poly(DL-lactic acid) with embedded lovastatin (Tom, J. W. et al. (1993), "Applications of Supercritical Fluids in the Controlled Release of Drugs," in *Supercritical Fluid Engineering Science*, pp. 238–257). In the RESS technique, particles of polymer may be made when a polymer is dissolved in a supercritical fluid (usually carbon dioxide) followed by rapid expansion of the fluid. This technique is limited in applicability to compounds that are soluble in the supercritical fluid. Since most drugs are not soluble in supercritical fluids and most polymers have very low solubility in supercritical fluids, the RESS process is not broadly applicable for drug encapsulation (McHugh, M. and Krukonis, V. (1994) *Supercritical Fluid Extraction*, Butterworth-Heinemann).

In the Precipitation by a Compressed Antisolvent (PCA) technique (also known as the Gas Antisolvent technique), a solid of interest is dissolved in a solvent and the resulting solution is sprayed into a compressed antisolvent (see, for example, U.S. Pat. Nos. 5,833,891 and 5,874,029). In this technique, the antisolvent and solvent are soluble, but the solid of interest is not soluble in the antisolvent. The antisolvent is believed to extract the solvent, precipitating particles of the solid of interest (Randolph, T. W. et al. (1993) Biotech. Prog. 9:429–435). Microparticles of insulin have reportedly been formed using this technique (Yeo, S.-D. et al. (1993), "Formation of Microparticulate Protein Powders Using a Supercritical Fluid Antisolvent," Biotech.

Bioeng. 41:341–346) and linear polymer microparticles have been formed using polymer starting materials (Bodmeier, R. et al. (1995), "Polymeric Microspheres Prepared by Spraying into Compressed Carbon Dioxide," Pharm. Res. 12(8):1211–1217; U.S. Pat. Nos. 5,833,891; 5,874,029).

There is a need for polymer particles with low residual solvent levels, high additive encapsulation efficiencies, and processes of making polymer particles that allow control of particle size and morphology, with low operating temperatures and efficient bulk production capability. Formation of polymer particles with degradable networks, whether by surface or bulk degradation, are also needed for controlled release of drugs, for example. In particular, highly crosslinked polymer networks with degradable chemistries are desired. Preferably, the extent of crosslinking or mesh size of such highly crosslinked polymer networks is controlled to tailor the release profile of the drug or other chemical to be released. In addition, there is a need for a process that produces polymer particles in situ from polymer precursors such as monomers or oligomers.

BRIEF SUMMARY OF THE INVENTION

In a general description of the invention, a method of forming polymer particles comprising exposing a composition comprising at least one polymer precursor, a solvent or solvent mixture, and an antisolvent or antisolvent mixture to photoradiation under conditions whereby particles are formed is provided. If the precursor is not photosensitive, at least one photoinitiator is present in the composition. The solvent is not required if the polymer precursor is liquid or liquifiable. If used, the solvent is chosen so that the polymer precursor is soluble in the solvent at the concentrations used, and the antisolvent and solvent are soluble in each other at the concentrations used. The polymer precursor is preferably insoluble in the antisolvent, but as long as nucleation and particle formation occur, any solubility condition may be present. Bioactive materials such as drugs may also be included in the composition.

Also provided is a method of forming polymer particles from a solution comprising contacting a solvent or solvent mixture and at least one polymer precursor with an antisolvent or antisolvent mixture under conditions whereby particles are generated; and exposing said particles to photoradiation, whereby polymer particles are formed. Preferably the polymer precursor is insoluble in the antisolvent or antisolvent mixture.

Also provided are polymer particles prepared by the methods of the invention that are between about 0.001 μm to about 200 μm in diameter. Each individual particle size and all intermediate ranges of particle size are included in the invention In one embodiment, particles are provided that are between about 0.1 μm and about 100 μm in diameter.

Linear and crosslinked polymer particles may be formed using the methods of the invention. Crosslinked polymer particles in which the crosslinked polymer forms a network are also provided. The mesh size of the network can be between about 10 Angstroms and about 500 Angstroms. Each individual mesh size and all the intermediate ranges of mesh sizes are included in the invention. For example, the mesh size can also be selected to be between about 10 Angstroms and about 100 Angstroms. Crosslinked particles comprising a multiplicity of converted carbon-carbon double bond functional groups are provided, wherein the conversion of the carbon-carbon double bonds is a measure of the extent of crosslinking. In one embodiment, the carbon-carbon double bond conversion in the particles is between about 20% and about 100%. Each individual value of carbon-carbon double bond conversion and all the intermediate ranges of carbon-carbon double bond conversion are included in the invention. For example, the carbon-carbon double bond conversion can be greater than about 70%.

Also provided is a method of forming polymer particles comprising: substantially dissolving at least one polymer precursor in a solvent or solvent mixture to form a solution; contacting said solution with an antisolvent or antisolvent mixture in which said polymer precursor is insoluble to form a composition comprising said precursor, and a substantially soluble mixture of said solvent or solvent mixture and said antisolvent or antisolvent mixture; and exposing said composition to sufficient photoradiation to initiate polymerization whereby polymer particles are formed.

Also provided is a method of forming polymer particles comprising: establishing a flow of antisolvent in an optically accessible chamber; contacting a solution comprising at least one polymer precursor and at least one polymerization initiator dissolved in a solvent or solvent mixture with said antisolvent under conditions whereby particles are formed; and exposing said particles to photoradiation whereby polymer particles are formed.

Also provided is a method for making crosslinked polymer particles with a desired double bond conversion amount comprising the steps of: exposing a composition comprising a polymer precursor, a non-aqueous solvent or solvent mixture, and an antisolvent or antisolvent mixture to photoradiation under conditions whereby crosslinked particles of the desired conversion amount are formed, wherein the antisolvent is a supercritical or near supercritical fluid in which the polymer precursor is not substantially soluble.

Also provided is a method for making crosslinked polymer particles having a desired network mesh size comprising the steps of:

selecting a polymer precursor;

determining a double bond conversion amount which corresponds to the desired network mesh size for the polymer;

exposing a composition comprising the polymer precursor, a non-aqueous solvent or solvent mixture, and an antisolvent or antisolvent mixture to photoradiation under conditions whereby crosslinked particles having the double bond conversion amount are formed, wherein the antisolvent is a supercritical or near supercritical fluid in which the polymer precursor is not substantially soluble and whereby the crosslinked particles have the desired network mesh size.

Also provided is a method of forming copolymers comprising: dissolving or suspending at least two polymer precursors or at least one polymer precursor and at least one polymer in a solvent or solvent mixture to form a solution; contacting said solution with an antisolvent or antisolvent mixture to form a composition comprising: said precursors or said precursor and polymer; a soluble mixture of said solvent or solvent mixture and said antisolvent or antisolvent mixture; and exposing said composition to photoradiation whereby copolymer particles are formed.

Copolymers may also be formed where at least one polymer precursor or at least one polymer are present in a solvent or solvent mixture, and at least one polymer precursor or at least one polymer are present in the antisolvent or antisolvent mixture, providing that at least one polymer precursor is present.

Also provided is a method of forming particles comprising a bioactive material and a polymer comprising: exposing a composition comprising at least one bioactive material, at least one polymer precursor and an antisolvent or antisolvent mixture to photoradiation under conditions whereby particles are formed.

Polymers formed may be erodable or nonerodable, biodegradable or nonbiodegradable and biocompatible or non-biocompatible. Polymer particles formed using the methods of the invention may be used for controlled release of a desired substance in an organism or system. Provided is a method of controlled release of a desired substance comprising: preparing polymer particles that comprise a degradable polymer and a desired substance; and exposing said polymer particles to conditions under which the polymer is degraded.

Methods of forming degradable particles comprising a degradable polymer and a pharmaceutical product comprising: exposing a composition comprising a solvent or solvent mixture, at least one polymer precursor capable of forming a degradable polymer, at least one pharmaceutical product, and an antisolvent or antisolvent mixture to photoradiation whereby polymer particles that contain a degradable polymer and a pharmaceutical product are formed are provided.

A pharmaceutical composition comprising polymer particles produced by the methods of the invention and a pharmaceutically acceptable carrier are also provided. Polymer particles comprising at least one bioactive material and at least one polymer are also provided.

Crosslinked polymer particles comprising a degradable polymer are also provided. Biodegradable crosslinked polymer particles are also provided. Crosslinked polymer particles further comprising at least one bioactive material are also provided.

An apparatus is provided for producing polymer microparticles which comprises: a reaction chamber; at least one inlet into said reaction chamber through which an antisolvent or antisolvent mixture, at least one polymer precursor insoluble in said antisolvent or antisolvent mixture, and a solvent or solvent mixture soluble in said antisolvent or antisolvent mixture pass into said chamber; and a light source optically connected to said chamber wherein during operation of the chamber said polymer precursor is polymerized. The apparatus may be used with a photosensitive polymer precursor, or a polymerization initiator may be added.

Advantages of this photopolymerization technique include morphological control through polymerization rate, process conditions, and initiation location. Processing time remains short while processing temperatures remain low. Low operating temperatures are important since many potential encapsulation additives degrade at moderate temperatures. In addition, particles formed using the method of the invention do not require further processing, for example solvent removal, before use.

Further objects and advantages of this invention will be apparent from a consideration of the drawings and description herein.

"Microparticles" as used herein means particles that are less than about 100 $\mu$m in diameter. "Nanoparticles" are particles that are less than about 1 $\mu$m in diameter. Both microparticles, nanoparticles and particles of other sizes may be produced by the methods of the invention by changing process parameters and choice of materials. Methods of changing the process parameters and materials are described herein, or determinable by one of ordinary skill in the art without undue experimentation.

"Polymer precursor" means a molecule or portion thereof which can be polymerized to form a polymer or copolymer. Polymer precursors include any substance that contains an unsaturated moiety or other functionality that can be used in chain polymerization, or other moiety that may be polymerized in other ways. Such precursors include monomers and oligomers. A "multifunctional monomer" is a monomer having two or more sites available for bonding to other molecules during polymerization. Preferred precursors include those that are capable of being polymerized by photoradiation. One class of polymer precursors of the invention are those that are insoluble in the antisolvent or antisolvent mixture. Another class of polymer precursors of this invention are photosensitive. If a polymer precursor that polymerizes photochemically is used (photosensitive polymer precursor), a separate photoinitator does not need to be used. Examples of photosensitive polymer precursors include tetramercaptopropionate and 3,6,9,12-tetraoxatetradeca-1,13-diene. Another class of precursors that may be used are radically polymerizable precursors. Another class of precursors that may be used are ionically polymerizable precursors. Another class of precursors that are useful in the invention are cationic precursors.

Some examples of precursors that are useful in the invention include ethylene oxides (for example, PEO), ethylene glycols (for example, PEG), vinyl acetates (for example, PVA), vinyl pyrrolidones (for example, PVP), ethyloxazolines (for example, PEOX), amino acids, saccharides, proteins, anhydrides, vinyl ethers, amides, carbonates, phenylene oxides (for example, PPO), acetals, sulfones, phenylene sulfides (for example, PPS), esters, fluoropolymers, imides, amide-imides, etherimides, ionomers, aryletherketones, olefins, styrenes, vinyl chlorides, ethylenes, acrylates, methacrylates, amines, phenols, acids, nitriles, acrylamides, maleates, benzenes, epoxies, cinnamates, azoles, silanes, chlorides, epoxides, lactones and amides. A preferred group of precursors includes all the above precursors with the exception of fluoropolymers.

Polymer precursors useful for producing crosslinked polymer particles include multifunctional monomers such as: vinyl acetates (for example, PVA), vinyl pyrrolidones (for example, PVP), vinyl ethers, olefins, styrenes, vinyl chlorides, ethylenes, acrylates, methacrylates, nitriles, acrylamides, maleates, epoxies, epoxides, and lactones. If a erosslinking agent is involved, polymers useful for producing crosslinked polymer particles include monomers such as: ethylene oxides (for example, PEO), ethylene glycols (for example, PEG), vinyl acetates (for example, PVA), vinyl pyrrolidones (for example, PYP), ethyloxazolines (for example, PEOX), amino acids, saccharides, proteins, arihychides, vinyl ethers, carbonates, phenylene oxides (for example, PPO), acetals, sulfones, phenylene sulfides (for example, PPS), esters, fluoropolymers, imides, amide-imides, etherimides, ionomers, aryletherketones, olefins, styrenes, vinyl chlorides, ethylenes, acrylates, methacrylates, amines, phenols, acids, nitriles, acrylamides, maleates, benzenes, epoxies, cinnamates, azoles, silanes, chlorides, epoxides, lactones and amides. Crosslinking agents include reactive groups having photocrosslinkable carbon-carbon double bonds attached to the ends of the polymer precursor chains. Such a carbon-carbon double bond can provide two sites available for bonding to other molecules. Suitable reactive groups having photocrosslinkable carbon-carbon double bonds include, without limitation, acrylates, methacrylates, alkenes and alkynes. Polymers having such reactive groups attached to the polymer precursor chains are termed "functionalized polymers". Polymer precursors useful for producing crosslinked polymer particles also include copolymers of the above monomers. Copolymers of the above monomers with degradable or erodable polymers may be used to obtain degradable or erodable crosslinked particles.

As used herein, "polymer" includes copolymers. "Copolymers" are polymers formed of more than one polymer precursor. Polymers that can be formed using the methods of this invention include those which are prepared from precursors that, in a preferred embodiment are soluble in a solvent that is soluble in an antisolvent and can be polymerized with light initiation. One class of polymers that may be prepared using the method of this invention includes those that are degradable, preferably biodegradable. Another class of polymers that may be prepared using the method of this invention includes those that are not degradable. Another class of polymers that may be prepared using the method of this invention includes those that comprise one or more degradable polymers and one or more nondegradable polymers. Another class of polymers that may be prepared using the method of this invention includes poly(lactides), poly(glycolides), and poly(lactide-co-glycolides). In a preferred embodiment of the invention, the polymers are degradable or erodable.

"Degradable or erodable polymers" are those that degrade upon exposure to some stimulus, including time. Degradable or erodable polymers include biodegradable polymers. Biodegradable polymers degrade in a biological system, or under conditions present in a biological system. Preferred biodegradable polymers degrade in an organism, preferably a mammal, and most preferably human. Examples of biodegradable polymers include those having at least some repeating units representative of at least one of the following: an alpha-hydroxycarboxylic acid, a cyclic diester of an alpha-hydroxycarboxylic acid, a dioxanone, a lactone, a cyclic carbonate, a cyclic oxalate, an epoxide, a glycol, and anhydrides. Preferred degradable or erodable polymers comprise at least some repeating units representative of polymerizing at least one of lactic acid, glycolic acid, lactide, glycolide, ethylene oxide and ethylene glycol.

A class of polymers included in this invention are biocompatible polymers. One type of biocompatible polymers degrade to nontoxic products. Specific examples of biocompatible polymers that degrade to nontoxic products that do not need removal from biological systems include poly (hydro acids), poly (L-lactic acid) or L-PLA, poly (D,L-lactic acid) or D,L-PLA, poly (glycolic acid) and copolymers thereof. Polyanhydrides have a history of biocompatibility and surface degradation characteristics (Langer, R. (1993) Ace. Chem. Res. 26:537–542; Brem, H. et al. (1995) Lancet 345:1008–1012; Tamada, J. and Langer, R. J. (1992) J. Biomat Sci.-Polym. Ed. 3:315–353).

Another class of polymers that may be prepared using the method of this invention include particles that are a suitable size for injection or administration orally or incorporated in a preparation suitable for oral administration. For oral or injectable delivery, it is preferred that most particles are less than 50 microns in diameter. Another class of particles that may be prepared using the method of this invention include those that are a suitable size for inhalation or pulmonary delivery. For pulmonary delivery, it is preferred that greater than about 90 weight percent of all solid particles in an administered pharmaceutical formulation are of a size smaller than about 10 microns and more preferably at least about 90 weight percent are smaller than about 6 microns, and even more preferably at least about 90 percent of all solid particles are from about 1 micron to about 6 microns. Particularly preferred for pulmonary delivery applications are particles of from about 2 microns to about 5 microns in size. Other classes of particles of suitable size for various applications are included in the methods of the invention.

Solvents useful in the invention include those that dissolve some portion of a polymer precursor and are preferably at least partially soluble in the antisolvent used. Preferably the solvent is miscible in the antisolvent or antisolvent mixture at the temperature and pressure of operation. Preferred solvents are not water. Some examples of preferred solvents include methylene chloride, methanol, toluene, propanol, ethanol, acetone, ethers, hexanes, heptane, tetrahydrofuran, methyl ethyl ketone, chloroform, carbon tetrachloride, butanone, dimethyl sulfoxide, isopropanol, ethyl acetate, methyl acetate, n-methylpyrrolidine, propylene carbonate, alkanes, and acetonitrile. If a liquid or liquidizable polymer precursor is used, a solvent is not necessary. One solvent or a mixture of solvents may be used.

Photoinitiators that are useful in the invention include those that can be activated with light and initiate polymerization of the polymer precursor. Preferred initiators include azobisisobutyronitrile, peroxides, phenones, ethers, quinones, acids, formates. Cationic initiators are also useful in the invention. Preferred cationic initiators include aryldiazonium, diaryliodonium, and triarylsulfonium salts. Most preferred initiators include Rose Bengal (Aldrich), Darocur 2959 (2-hydroxy-1-[4-(hydroxyethoxy)phenyl]-2-methyl-1-propanone, D2959, Ciba-Geigy), Irgacure 651 (2,2-dimethoxy-2-phenylacetophenone, I651, DMPA, Ciba-Geigy), Irgacure 184 (1-hydroxycyclohexyl phenyl ketone, I184, Ciba-Geigy), Irgacure 907 (2-methyl-1-[4-(methylthio)phenyl]-2-(4-morpholinyl)-1-propanone, I907, Ciba-Geigy), Camphorquinone (CQ, Aldrich), isopropyl thioxanthone (quantacure ITX, Great Lakes Fine Chemicals LTD., Cheshire, England). CQ is typically used in conjunction with an amine such as ethyl 4-N,N-dimethylaminobenzoate (4EDMAB, Aldrich) or triethanolamine (TEA, Aldrich) to initiate polymerization.

The wavelengths and power of light useful to initiate polymerization depends on the initiator used or the wavelength (or wavelengths) will activate the photosensitive precursor. A combination of photosensitive precursor(s) and photoinitiator(s) may be used. When Rose Bengal is used as the initiator, a visible light source is preferably used. Light used in the invention includes any wavelength and power capable of initiating polymerization. Preferred wavelengths of light include ultraviolet or visible. Any suitable source may be used, including laser sources. The source may be broadband or narrowband, or a combination. The light source may provide continuous or pulsed light during the process.

Chamber windows made from various materials may be used in the method of this invention. In addition, a filter may used to block a wavelength from reaching the chamber, or allow a selected wavelength or wavelengths of light to reach the chamber. The chamber windows themselves may act as this filter, or a separate filter or filters may be used in conjunction with the chamber windows.

In one embodiment, a broadband light source may be used, and by selecting chamber window compositions and/or filter combinations, the selected wavelength or wavelengths of light may pass through the chamber. Light of different selected wavelengths may pass through the same chamber at various locations. This feature may be used to activate more than one photoinitiator.

As used herein, "antisolvent" is a substance in which the polymer precursor is substantially not soluble. It should be understood that it is possible that the antisolvent may be capable of dissolving some amount of the precursor without departing from the scope of the present invention. The antisolvent is, however, preferably incapable of dissolving a significant portion of the precursor such that at least a significant portion of precursor is, in effect, not soluble in the antisolvent. Preferably, the antisolvent precipitation is conducted under thermodynamic conditions which are near critical or supercritical relative to the antisolvent fluid. The antisolvent preferably comprises any suitable fluid for near critical or supercritical processing. These fluids include carbon dioxide, ammonia, nitrous oxide, methane, ethane, ethylene, propane, butane, pentane, benzene, methanol, ethanol, isopropanol, isobutanol, fluorocarbons (including chlorotrifluoromethane, monofluoromethane, hexafluoraethane and 1,1-difluoroethylene), toluene, pyridine, cyclohexane, m-cresol, decalin, cyclohexanol, o-xylene, tetralin, aniline, acetylene, chlorotrifluorosilane, xenon, sulfur hexafluoride, propane and others. Carbon dioxide, ethane and propane are preferred antisolvents. Most preferably, carbon dioxide is used as the antisolvent. One antisolvent, or a mixture of different antisolvents may be used.

As used herein, "supercritical or near supercritical fluid" means a substance that is above its critical pressure and temperature or is substantially near its critical pressure and temperature.

Components that are "contacted" with each other refers to two or more components physically near each other. Components that are contacted with each other are preferably in intimate contact with each other so that they may react with each other or affect each other. Contact may include emulsions or microemulsions.

A "bioactive" material is any substance which may be administered to any biological system, such as an organism, preferably a human or animal host, and causes some biological reaction. Bioactive materials include pharmaceutical substances, where the substance is administered normally for a curative or therapeutic purpose. The bioactive material may comprise a protein or other polypeptide, an analgesic or another material. In one embodiment, the bioactive material has a molecular weight less than 1000 Da. Suitable bioactive material includes, without limitation, tacrine, erythromycin, erythromycin estolate, and erythromycin ethylsuccinate.

A "polymer shell" may be a continuous coating of polymer over some substance, but the coating is not required to be continuous. The polymer shell may have nonhomogeneous regions where there is no coating, or regions where the coating is thicker than in other areas. The polymer shell may be composed of different materials. Preferably, the polymer shell is a homogeneous coating with uniform thickness. "Encapsulated" is intended to indicate a substance, such as a bioactive material, is homogeneously distributed throughout the polymer.

"Linear polymers" are those polymers that are composed of individual polymer chains that do not have bonds connecting the chains. "Crosslinked polymers" are those polymers that have bonds between polymer chains. Branched polymers are also included in the invention.

"Soluble" does not necessarily mean completely soluble. As long as some portion of one substance dissolves in another substance, the substances are soluble in each other. Likewise, "insoluble" does not necessarily mean that no amount of one substance will dissolve in another substance.

A "composition" of substances is not intended to mean the substances are soluble or miscible with each other, or react with each other. A "composition" is merely intended to mean all listed substances are present.

DETAILED DESCRIPTION OF THE INVENTION

Figure 1:
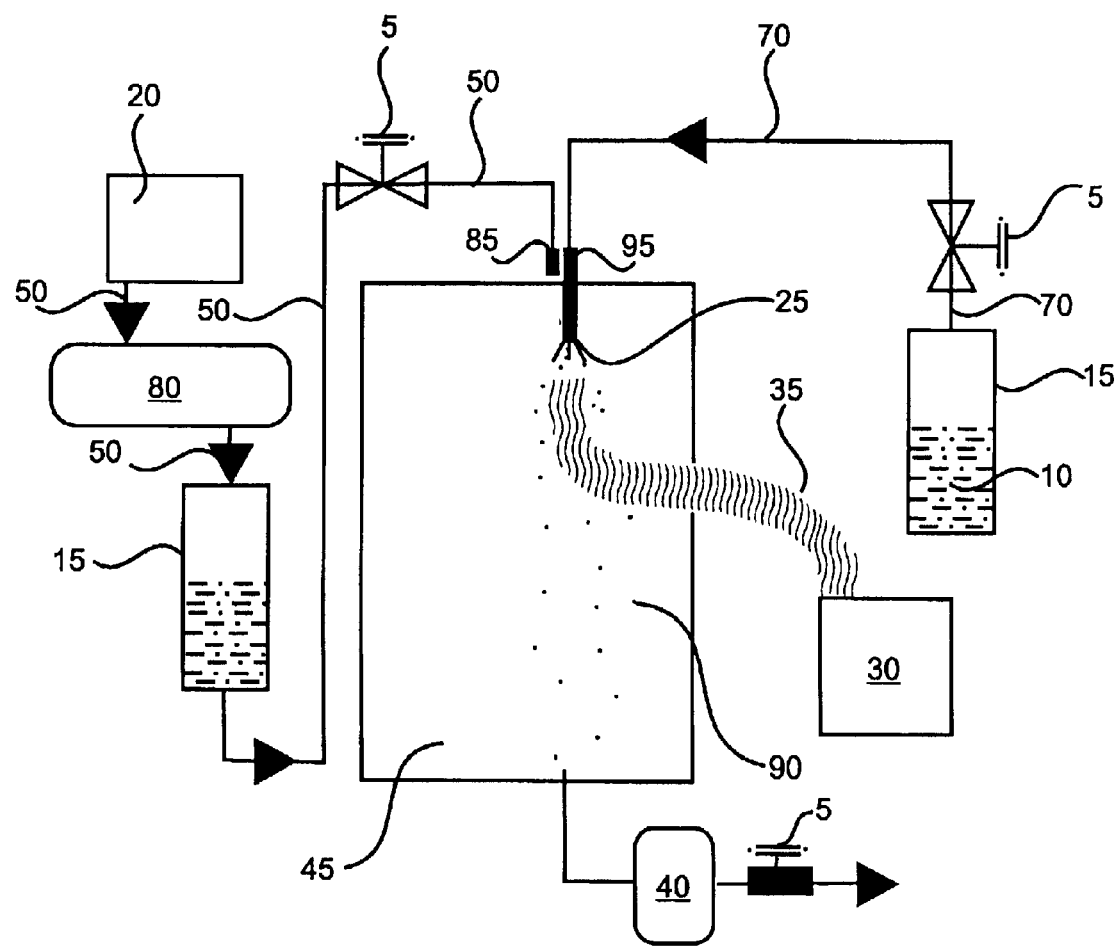
FIG. 1 is a schematic diagram of a photopolymerization system.

A process for photopolymerizing polymer particles in-situ with antisolvent precipitation is provided. Photopolymerization occurs when solutions of polymer precursor and solvent are exposed to light of sufficient power and of a wavelength capable of initiating polymerization while being contacted with an antisolvent at reduced temperature ($T_r$) and pressure ($P_r$). The polymerization may be initiated by a polymerization initiator activated by light, or a photosensitive polymer precursor may be used. If a photosensitive polymer precursor is used, a separate photoinitiator is optional. The polymer precursor and solvent solution may be homogeneous, but that is not required. This type of polymerization results in particles with a wide range of morphologies, sizes and physical characteristics adjustable by changing the process conditions. The polymer particles produced by the methods of the invention do not require any further processing (for example solvent removal) before they may be used.

Not wishing to be bound by any theory, it is believed that the chamber conditions coupled with the antisolvent properties (high diffusivity, low viscosity, and high solvating capacity) facilitates the extraction of the solvent from the solution leaving mostly precursor and initiator (if used). At the same time, these precursor/initiator particles receive photons from the UV source, initiating the polymerization.

The reduced temperature is the ratio of the operating temperature over the critical temperature for the antisolvent.

$$T_r = \frac{T_{operating}}{T_{critical}}$$

The reduced pressure is the ratio of the operating pressure over the critical pressure for the antisolvent.

$$P_r = \frac{P_{operating}}{P_{critical}}$$

In the methods of the invention, $T_r$=0.7 to 1.3, preferably $T_r$=0.9 to 1.1. In the methods of the invention, $P_r$=0.5 to 2, preferably, $P_r$=0.75 to 1.5.

The precursor/initiator/solvent should remain at a temperature such that the initiators (if used), precursors and any desired additives are not degraded to an extent that is unacceptable for the particular application. The methods of this invention may be used where the antisolvent is not at reduced pressure and temperature to produce polymer particles, as long as particle formation occurs. The methods of the invention may also be used to produce polymer particles when the solvent or solvent system used is not completely miscible in the antisolvent or antisolvent mixture, or when the precursor is soluble to some extent in the antisolvent or antisolvent mixture.

Polymers with many different morphologies and physical properties may be produced using the methods of this invention. The morphology changes in polymers formed by changing conditions in the PCA experiment have been studied (Dixon, D. J. and Johnston, K. P. (1993), "Formation of Microporous Polymer Fibers and Oriented Fibrils by Precipitation with a Compressed Fluid Antisolvent," J. Appl. Polym. Sci. 50:1929–1942).

Polymers with improved mechanical strength, polymer-encapsulated bioactive materials where the biomaterial has controlled transport properties through the polymer, and polymers that are capable of degrading or remaining substantially intact in a given system, for example an organism such as a human or other mammal, may be prepared using the methods of this invention. Nondegradable polymers may be formed using the methods of this invention. Polymer particles may be formed using the methods of the invention for use in many applications such as agricultural controlled release of fertilizer, use as fillers, and other applications. In addition to polymer particles, polymer fibers and porous polymer particles, for example, are achievable by changing one or more process parameters such as the solvent flow rate, polymer precursor type and functionality, photoinitiator concentration, initiation rate, chamber operating temperature or pressure, among other parameters.

For example, increasing the concentration of polymer precursor in the solution increases the diameter of the polymer particles formed. In addition, initiating polymerization some distance after the particles have been formed increases the diameter of the polymer particles formed. The diameter of the polymer particles formed can be increased by manipulating the nozzle size, increasing the concentration of monomer, increasing the temperature. Polymer fibers as opposed to more spherical particles can be formed by using slower flow rates of the precursor/initiator/solvent.

Copolymers may also be made using this method, as well as bioerodable polymer particles which can be used, for example, in controlled release applications.

Polymers with crosslinked polymer networks may also be formed using the methods of this invention. In a photoinitiated process, the extent of crosslinking may be controlled by, for example, controlling the carbon-carbon double bond or other reactive functional group concentration in the polymer precursor, the intensity of the light source, the time of exposure to the light source, and the photoinitiator concentration (if present). The time of exposure to the light source, or residence time, is controlled by the combination of the antisolvent and solution flow rates. The extent of cross-linking is preferably large enough to provide gelation of the polymer and prevent agglomeration of the particles once they are formed. In general, less reactive polymers will require more exposure time, higher light intensity, and a higher photoinitiator concentration. Those skilled in the art can assess the relative reactivities of monomers based on their molecular weights and functional groups.

For precursors having C=C functional groups, formation of crosslinks between molecules involves conversion of C=C bonds to C—C bonds. Bonds which have been converted from C=C double bonds can be termed "converted C—C double bonds." Similarly, those functional groups containing C=C double bonds which have been converted to C—C single bonds can be termed "converted functional groups", e.g. converted acrylate or methacrylate groups. The extent of crosslinking can be measured by FTIR analysis of the double bond conversion in the polymer particles (referenced to double bond measurements of the unreacted precursor) or by other methods as known to the art. Uncertainty in this method of double bond conversion can be ±10%, but is typically ±5%. Similar measures of the extent of crosslinking are known to the art for precursors having other types of functional groups.

For polymer networks which swell in solvent, the mesh size of the polymer network in the particles for a given extent of double bond conversion can be estimated from network mesh sizes for a bulk polymer having the same extent of double bond conversion. Mesh sizes for the bulk polymer can be calculated from measurements of the swelling of the bulk polymer as described by Lu and Anseth, (2000), "Release Behavior of High Molecular Weight Solutes from Poly(ethylene glycol)-Based Degradable Networks", Macromolecules, pp 2509–2515.

For polymer networks which do not swell in solvent, the mesh size of the particles can be estimated statistically assuming an ideal network and a monodisperse monomer molecular weight. For macromers having C=C functional groups which are 100% converted to C—C kinetic chains or crosslinks, the sum of the bond lengths of the repeating unit (excluding side groups) can multiplied by the number of monomer units to obtain the length of one side of the mesh. The length of the other side of the mesh can be estimated to be the same as the kinetic chain length or C—C bond length. With an ideal network (100% conversion, no cyclization) the mesh size is the average of these 2 lengths. To calculate for other conversions, the system can be idealized further. For example, for 50% conversion, it can be estimated that every other monomer unit, there will be a kinetic chain link, so the length of one side of the mesh can be estimated as twice the sum of the bond lengths of the starting monomer multiplied by the number of monomer units. The length of the other side of the mesh can be estimated as the C—C bond length as before.

Additives of various sorts may be added to the precursor/initiator/solvent solution or the antisolvent. These additives may include, but are not limited to: plasticizers, coloring agents, encapsulation agents, bioactive materials such as drugs of various kinds, and other inert or bioactive particles. As used herein, encapsulation efficiency refers to the amount of drug encapsulated into a quantity of particles (which can be calculated from release data) divided by the amount of drug loaded into an equivalent quantity of precursor. The methods of the invention allow improved encapsulation efficiency of additives such as bioactive materials by allowing a wide range of polymer precursors to be used. The polymer precursor can then be selected which is compatible with the drug. For example, a hydrophobic bioactive material can be paired with a relatively hydrophobic polymer.

The degradability of these materials can further be controlled by varying polymer composition and morphology. This permits tuning degradation devices to match a desired release rate or release profile. Homogeneous encapsulation of a drug, for example, into polymer particles in a single manufacturing step is possible using the methods of this invention. Changing the size and morphology of the degradable particles allows control over the dose and duration of the drug delivery.

A variety of embodiments of the invention are possible. For example, one drug may be encapsulated in a polymer particle using the methods of the invention. Then, a second polymer precursor, initiator and drug may be used to encapsulate a second drug over the first particle. This will result in a particle that has two or more different bioactive materials with different release profiles. This is useful in a variety of different therapeutic applications.

Methods of determining appropriate dosages for bioactive materials are well known to one of ordinary skill in the art. Polymer particles and compositions comprising bioactive materials are administered by methods well known in the art, or by adapting methods well known in the art.

This invention is useful for other controlled release of materials other than drugs. Other applications include controlled release of fragrances and pesticides. Particles may be made using the methods of the invention that release corrosion inhibitors over a specified time. This may be useful in pipeline applications. Other uses are readily apparent to one of ordinary skill in the art without undue experimentation.

To circumvent potential problems associated with solubilizing a hydrophilic drug in an organic solvent such as microphase separation and consequent burst effects, the photopolymerization technique described herein can be combined with a solubilization technique known as hydrophobic ion-paring (HIP) to form homogeneous solutions of drug, monomer and initiator in an organic solvent and photopolymerized drug-encapsulated microparticles. HIP is described in U.S. Pat. Nos. 5,981,474 and 5,771,559, hereby incorporated by reference to the extent not inconsistent with the disclosure herein. HIP is a technique whereby ionic pharmaceutical agents can be directly solubilized in organic solvents. HIP consists of pairing charges on the molecule with oppositely charged, hydrophobic organic ions, effectively increasing the molecule's solubility in low-dielectric organic solvents. The photopolymerization method described herein may be used in combination with HIP to encapsulate a therapeutic agent in polymer particles.

Parts per billion residual solvent levels have been obtained for PCA processing of linear poly(lactic) acid, in which the particles are washed with several volumes of $CO_2$ after processing (Falk and Randolph (1998) Pharmaceutical Research, 15, 8, 1233–1237). If the particles of the present invention are washed with supercritical fluid such as $CO_2$ after processing, residual solvent levels can be reduced below 1%.

Apparatus for Polymerization Experiments

FIG. 1 illustrates an apparatus of this invention for providing polymer particles. The apparatus has a chamber (45) with one or more inlets (85, 95) that allow substances to pass into chamber (45). In a particular embodiment, antisolvent (20) is connected to optional oxygen scrubber (80) through connecting tubing (50). Oxygen scrubber (80) is connected to pump (15) through connecting tubing (50). Pump (15) is connected to valve (5) with connecting tubing (50). Valve (5) is connected to inlet (85) through connecting tubing (50). Inlet (85) allows antisolvent (20) to enter chamber (45). Pump (15) is used to pump solution (10) comprising one or more polymer precursors, one or more initiators and one or more solvents to valve (5) through connecting tubing (70). Solution (10) is pumped to inlet (95) through connecting tubing (70). Inlet (95) allows solution (10) to enter injector (25) inside chamber (45). Light pipe (35) passes light from light source (30) into chamber (45). After polymer particle formation, particles (90) pass out of chamber (45) to filter (40) and valve (5).

The embodiment described by FIG. 1 illustrates more than one inlet (85 and 95). In an alternative embodiment, the antisolvent and solution pass into the chamber through one inlet. The precursor/initiator/solvent may also be sprayed into a stream of antisolvent or antisolvent mixture. In another alternative embodiment, there are multiple inlets for various components.

In operation, the following preferred procedure is used. Antisolvent (20) is optionally deoxygenated with oxygen scrubber (80). Antisolvent (20) is pumped with one or more pumps (15) through connecting tubing (50) to valve (5). Antisolvent (20) is then pumped into optically accessible high pressure chamber (45) through inlet (85). The flow rate of antisolvent (20) into chamber (45) is typically about 25 ml/min. An optional heating or cooling source (not shown) may be positioned in any suitable location to provide any necessary heating or cooling to the antisolvent, the chamber, or any part of the apparatus or any component thereof. Antisolvent (20) is preferably pressurized and heated so that it is at or above its critical pressure and critical temperature. Chamber (45) is allowed to equilibrate at the desired temperature and pressure (preferably at or above the critical temperature and pressure of the antisolvent). At least one polymer precursor and at least one photoinitiator are dissolved or suspended in a suitable solvent to form solution (10). Solution (10) is pressurized to the desired pressure with pump (15). Solution (10) is pumped through connecting tubing (70) to valve (5) and pumped through connecting tubing (70) to inlet (95). Antisolvent (20) can be co-flowed coaxially with solution (10). Solution (10) passes through inlet (95) into injector (25) into chamber (45). In one embodiment, injector (25) is a stainless steel tube with a 100 μm opening which injects solution (10) into chamber (45). In another embodiment, injector (25) is any type of injector known in the art, including ultrasonic nozzles and laser drilled holes. Many different nozzles may be used, including a stainless steel capillary tube, a quartz capillary tube, a sonicated nozzle, and a converging diverging nozzle with a premixing chamber. The injector and inlet are not required to be separate components. The flow rate of solution (10) through injector (25) is typically about 0.1 to about 1 ml/min. Light source (30) provides the necessary photons to initiate photopolymerization at a desired distance (in one embodiment, 2–3 cm) below solution injector (25). In one embodiment, light source (30) is a ultraviolet or visible light source at about 800 to about 6300 mW/cm$^2$ (30). The light is transferred from light source (30) into chamber (45) using any suitable means, including optical fiber (35). Particles (90) may be collected by any suitable means, including the use of filter (40). A 0.2 μm filter is used in one embodiment, but any suitable pore size may be used. The size of the pores of the filter needed will depend on the size of the particles formed and the desired size of particles collected. Particles may be transferred from filter (40) through valve (5).

The chamber itself in a preferred embodiment is a 5"×4"× 9" long stainless steel chamber with a volume of 100 ml. Tempered borosilicate windows (3.5" long each) are used. The chamber weighs about 50 pounds. Other embodiments of the chamber may be used.

Alternate Apparatus for Continuous Processing

Figure 2:
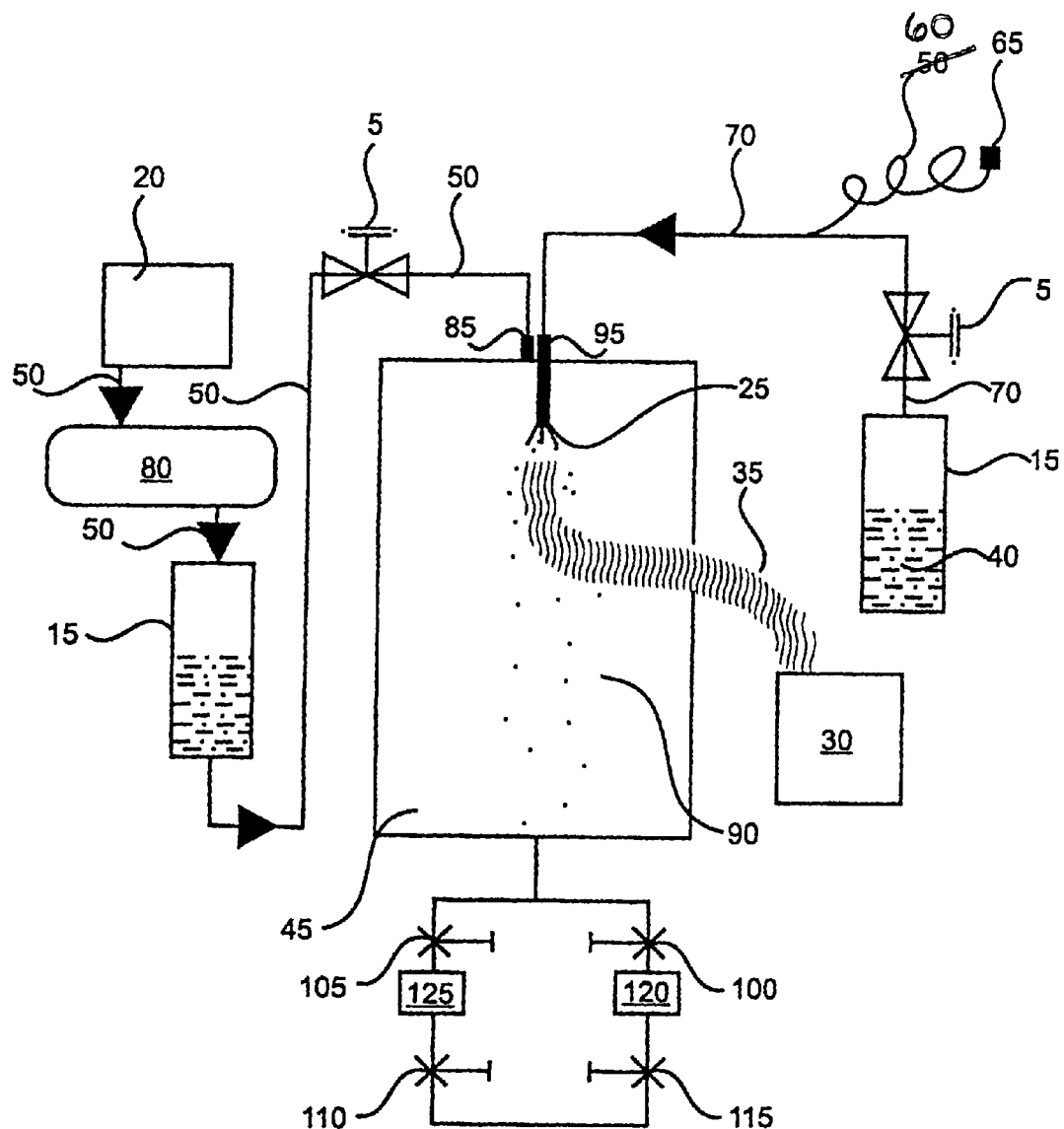
FIG. 2 is a schematic diagram of a continuous photopolymerization system.

Alternatively, the apparatus may be operated in a continuous mode. This is shown in FIG. 2. In this embodiment, injector loop (60) with injection port (65) such as those used in an HPLC apparatus may be added to the apparatus to allow processing of multiple solutions or multiple samples of the same solution without the time consuming pressurizing and depressurizing cycles that would otherwise be required. In this embodiment, a flow of solvent (40) is maintained through connecting tubing (70), a flow of anti-solvent (20) is maintained through connecting tubing (50), and a solution of polymer precursor/initiator and solvent is injected into the solvent flow through injection port (65).

A series of valves and filters may be used to enable particle collection without depressurizing the system. This is also shown in FIG. 2. The flow path exiting the chamber is split. Particles may be collected on filter (125) by closing valve (100) and opening valve (105). By closing valve (105) and opening valve (100), particles may be collected on filter (120). While particles are being collected on filter (120), filter (125) may be replaced. This way particles may be collected continuously by routing the flow. This allows a continuous, not batch, process to be maintained, and greater amounts of polymer particles may be produced.

The apparatuses described above are only some of the possible apparatuses that may be used to carry out the invention. Other embodiments of the apparatus or components of the apparatus will be readily apparent to those of ordinary skill in the art. For example, the solution of polymer precursor(s) and photoinitiator(s) may pass into the chamber through other diameter injectors or injector types other than those mentioned specifically. The solution of polymer precursor(s) and photoinitiator(s) may be optionally heated or cooled in any suitable location. Any suitable light source may be used, and any suitable method of bringing light to the chamber may be used. The light is brought into the chamber at any desired location. The range of possible modifications is well known to one of ordinary skill in the art without undue experimentation.

The invention will be further understood by reference to the following examples intended as illustrations, not limitations.

EXAMPLES

Preparation of Methacrylated Sebacic Anhydride

The monomer, methacrylated sebacic anhydride (MSA), was prepared by combining 40 g sebacic acid (Aldrich) with 88 ml methacrylic anhydride (Aldrich) and refluxing for approximately 1 hour. This process, shown in Scheme 1, converts the dicarboxylic acid to the anhydride monomer which is subsequently dissolved in dry methylene chloride (Fisher) and precipitated in petroleum ether (Aldrich) for purification and recovery (U.S. Pat. No. 4,789,724).

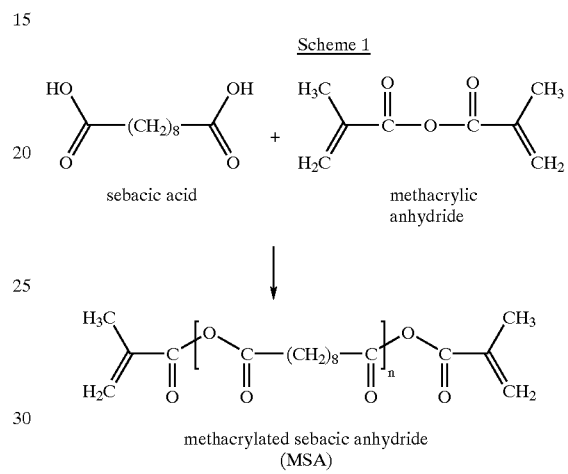

Scheme 1 methacrylated sebacic anhydride (MSA)

Proton NMR spectroscopy (Varian VXR-300S) was used to verify the existence of the characteristic methacrylate end-capped =CH$_2$ protons that give peaks at 5.8 and 6.2 ppm. Infrared spectroscopy (IR) shows the presence of the methacrylate double bond group at 1635 cm$^{-1}$ and confirmed the conversion of the acid groups to the anhydride (Muggli, D. S. et al. (1998) Macromolecules 31:4120–4125). After forming the dimethacrylated monomeric anhydride, the monomer can be oligomerized through a condensation polymerization under vacuum at a temperature of 60° C. A ratio of the integrated area of the =CH$_2$ proton peaks to the internal protons in the MSA backbone from the NMR analysis suggests a number average degree of oligomerization of ~6 repeat units.

Initiator Selection

Figure 3:
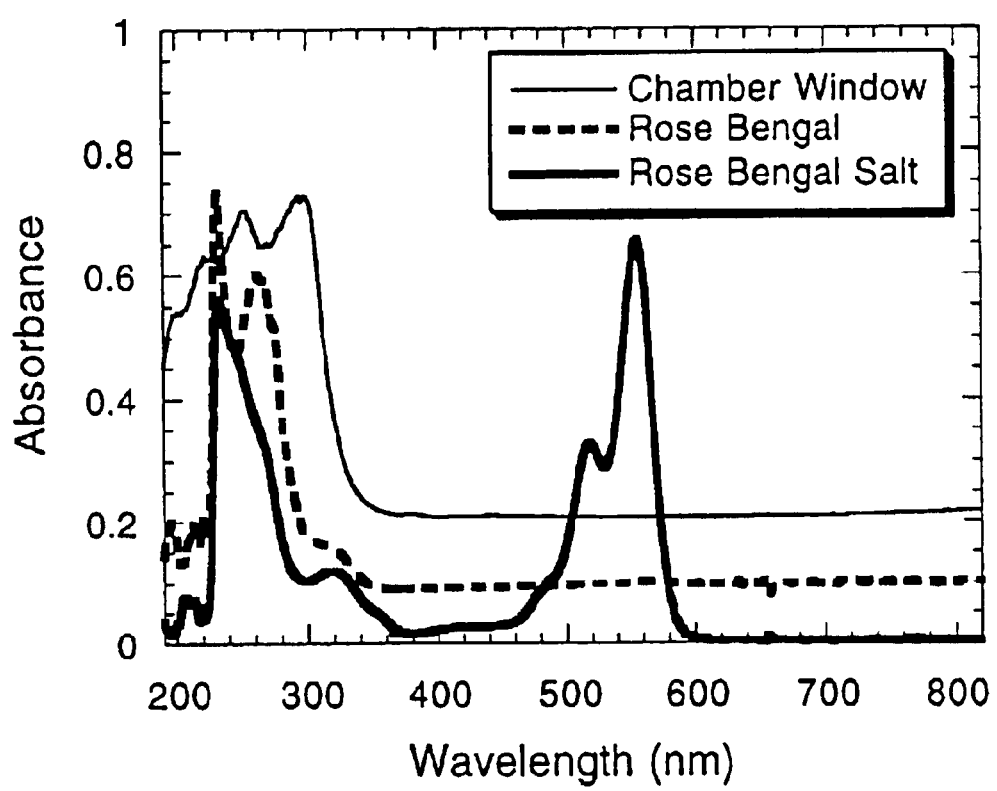
FIG. 3 is a UV-vis spectrum of the chamber window, Rose Bengal ($3.8 \times 10^{-6}$ wt percent) in methylene chloride and Rose Bengal bis(triethylammonium) salt (0.001 wt percent) in methylene chloride.

The photoinitiators used in these experiments were Rose Bengal and Rose Bengal bis(triethyl ammonium) salt obtained from Aldrich, although other initiators may be used. Interestingly, the Rose Bengal and its ammonium salt have dramatically different absorbance spectra in methylene chloride. FIG. 3 shows that the large peak at ~550 nm seen in the Rose Bengal salt is not present in Rose Bengal. Since the chamber window used in these experiments absorbed wavelengths below 350 nm, visible light initiators were used, and the triethyl ammonium Rose Bengal salt, whose absorbance spectrum is shown in FIG. 3 was used in these experiments.

Particle Production.

5–20 wt % methacrylated sebacic anhydride was dissolved in methylene chloride along with 2% photoinitiator by monomer weight. The chamber was pressurized with deoxygenated CO$_2$ by two ISCO compressed gas pumps and allowed to equilibrate to the desired temperature and pressure. The monomer-solvent solution was then pressurized to the desired pressure by a third ISCO pump. The solution was injected into the pressurized chamber environment at a constant flow rate (1 ml/min) through the nozzle while the $CO_2$ flowed at a constant rate of 25 ml/min. A high powered light source (1–4 $W/cm^2$) (EFOS, Novacure) with a visible filter (350–650 nm) and a fiber optic liquid light guide was used to initiate the photo-polymerization below the nozzle. A 5 cm Light Line (EFOS) was used to spread out the beam from the light source to give a longer initiating time in the chamber.

After spraying and polymerization, the system was allowed to settle for half an hour before slow depressurization (~30 min) at the operating temperature. This slow depressurization increased the number of particles collected on the scanning electron microscopy (SEM) stub mounted inside the chamber. After depressurization, samples were also taken from both the inside of the chamber and the 0.2 $\mu$m filter. The resulting particles were examined using SEM to determine their size and morphology.

The poly (methacrylated sebacic anhydride) (PMSA) particles were also viewed using a fluorescence microscope (data not shown). The Rose Bengal photoinitiator is a fluorescent dye for the microparticles, with an excitation peak at 540 nm and an emission band between 550–600 nm, so the distribution of photoinitiator in the polymerized particles can be visibly characterized.

Figure 4:
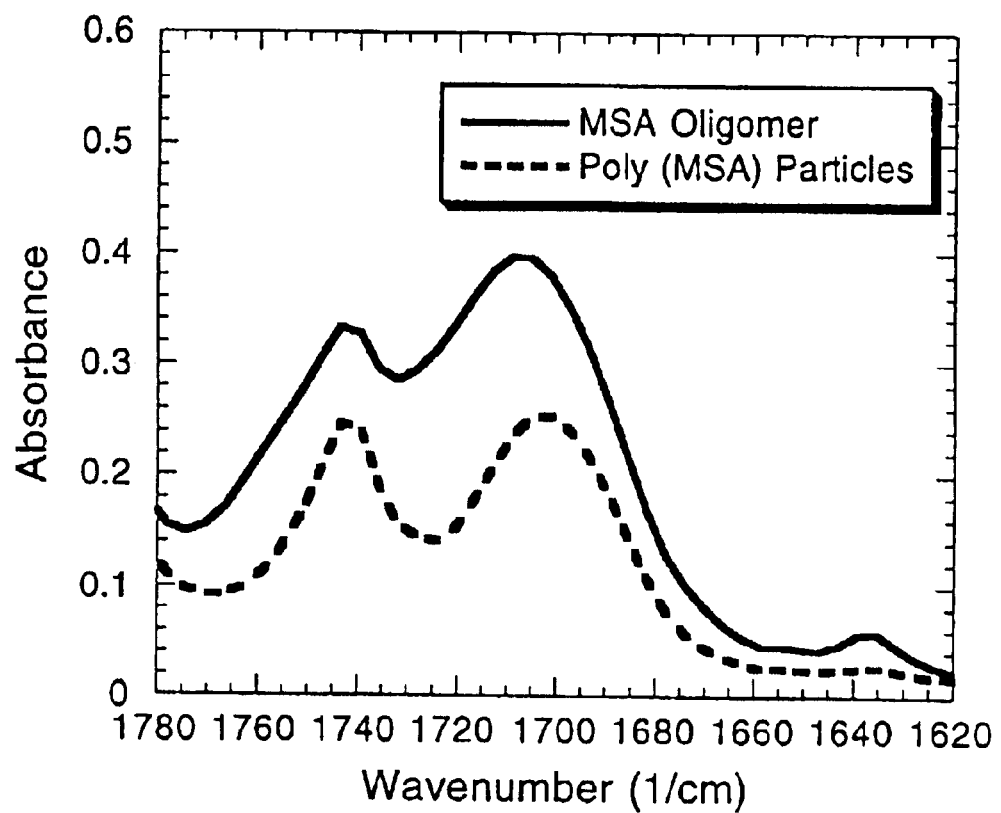
FIG. 4 is a Fourier transform infrared (FTIR) spectra of methacrylated sebacic anhydride oligomer and poly (methacrylated sebacic anhydride).

Polymerization of the multifunctional anhydride monomers during the particle processing was confirmed through Fourier transform infrared (FTIR) spectra of the particles compared to the oligomer (FIG. 4). The peak at 1635 $cm^{-1}$ is assigned to the carbon-carbon double bond stretching in MSA and is largely reduced in relative intensity in the spectrum of (PMSA). The reduction of the peak to immeasurable levels further suggests nearly complete reaction possibly due to added mobility from the solvent.

Figure 5:
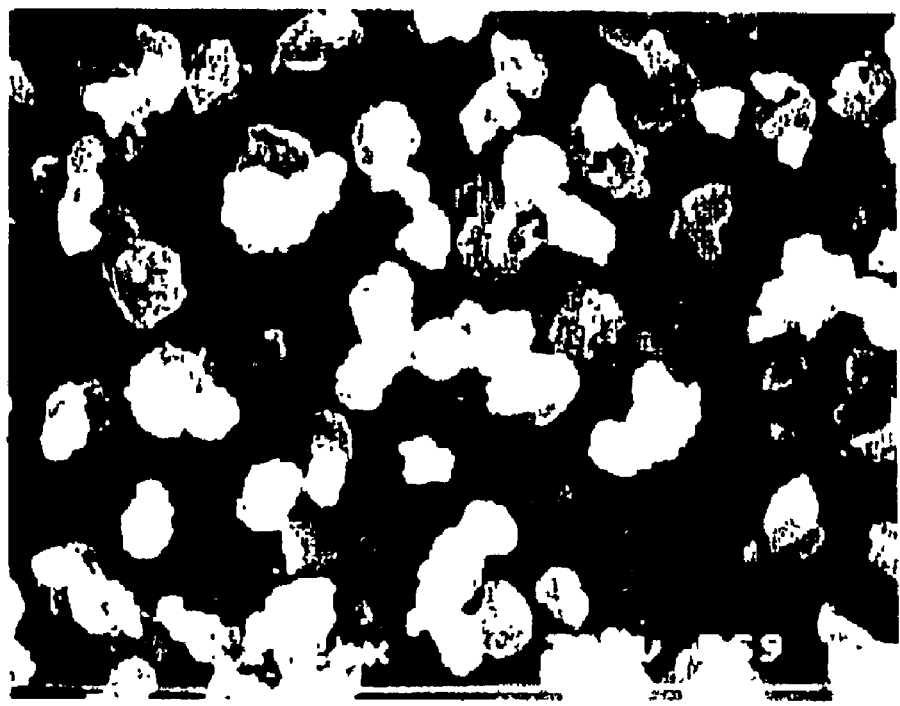
FIG. 5 is a scanning electron microscopy (SEM) photograph of poly(methacrylated sebacic anhydride) microparticles precipitated by spraying and photopolymerizing a 10 wt % MSA solution through a 100 $\mu$m capillary nozzle into $CO_2$ at a temperature of 37° C. and pressure of 8.5 MPa.

FIG. 5 is a scanning electron microscopy (SEM) photograph of the poly (methacrylated sebacic anhydride) microparticles magnified 2200 times. These particles were sprayed as described above with a nozzle consisting of a 100 $\mu$m stainless steel capillary tube and an operating temperature of 37° C. The particles, although not perfectly spherical, exhibit a round or substantially spherical morphology with diameters ranging from 5 to 15 $\mu$m. This narrow size distribution is an important advantage of this processing technique since many applications of polymer microparticles require a narrow size distribution, especially biomedical applications where the body may absorb or reject the particles based on their size. The size distribution can also control the release kinetics.

Cloud Point Measurements

Cloud point experiments were performed to measure the solubility of the monomer solution in $CO_2$ at the initial operating conditions of 8.5 MPa and 37° C. A 3 L view cell was injected with a methylene chloride/MSA solution and a pump system insured complete mixing. At a constant temperature of 37° C., the cell was then pressurized with $CO_2$ using a hand pump up to ~95 bar. Next, the cell was slowly depressurized and the pressure at which the monomer solution mixture became visibly insoluble was recorded. The process was repeated three times for each MSA solution concentration and the cloud point pressures were averaged. These results are shown in FIG. 6.

Figure 6:
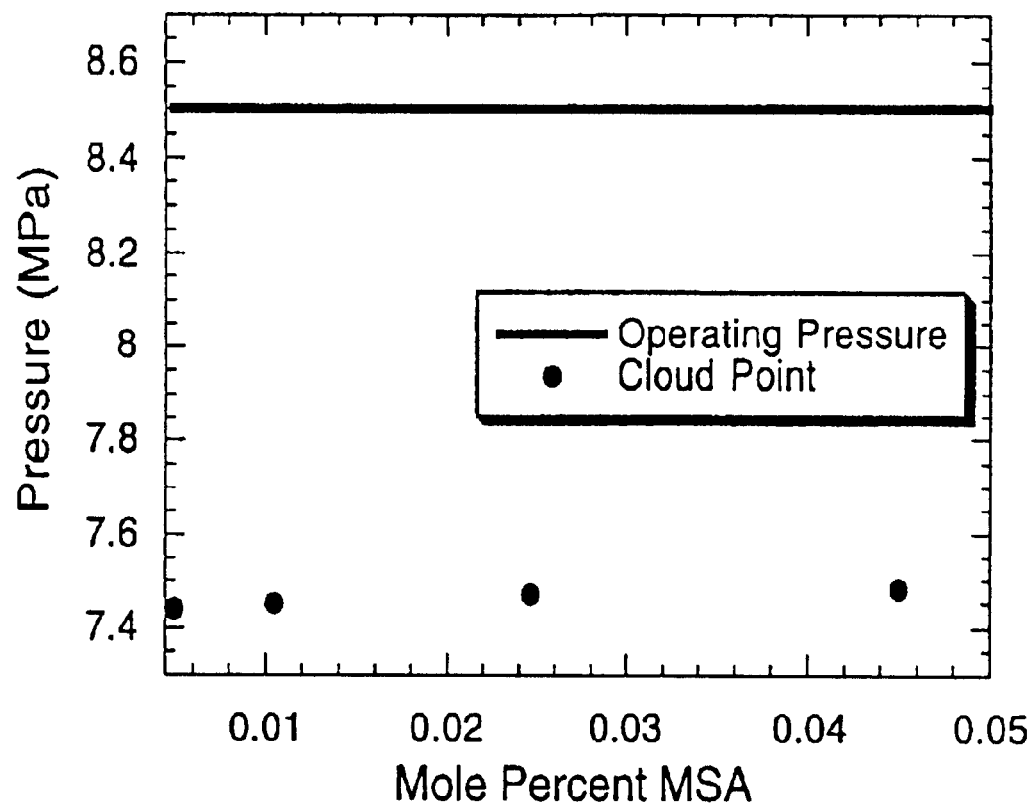
FIG. 6 shows cloud point data for various molar concentrations (consistent with general operating conditions) of MSA monomer in methylene chloride at 37° C.).

FIG. 6 shows the cloud point pressure for this system, which is far below the initial operating pressure implying that the monomer solution is in a gaseous state at the initial operating conditions of 37° C. and 8.5 MPa. If the monomer remains in a gaseous state during photopolymerization, this would significantly dilute the monomer concentration and decrease the rate of polymerization and the probability of microparticle formation during the exposure time. A rapid polymerization rate and a low gel point conversion are desired for this system because the exposure time after atomization is short ($4 \times 10^{-2}$ sec). To circumvent this problem, the operating temperature was lowered to 25° C. such that the operating pressure was below the cloud point. After this adjustment, the monomer polymerized in the chamber and particles with a high C=C conversion were obtained.

Figure 7:
FIG. 7 is an SEM micrograph of PMSA precipitated by spraying and photopolymerizing a 5 wt % MSA solution through an ultrasonic atomizing nozzle into $CO_2$ at a temperature of 25° C. and pressure of 8.5 MPa.

FIG. 7 is an SEM micrograph of PMSA particles magnified 2000 times that were precipitated from a 5 wt % MSA solution using an ultrasonicated atomizing nozzle and an operating temperature of 25° C. Consistent product particles with the same size (again 5 to 15 $\mu$m) and morphology were formed at these operating conditions. Although not spherical, the particle morphology is strikingly similar to the cusped surfaces formed in low pressure PCA with linear polymers. These particle surface features are speculated to be a result of slow drying or surface-only polymerization. A surface-only polymerization would likely result in these flat, petal-like particles because polymerization would occur on one face of the droplet which might give the "dark" side of the droplet time diffuse into the $CO_2$ phase. Monomer-solvent solubilities and operating conditions may be manipulated to obtain solid, spherical particles.

Figure 8A:
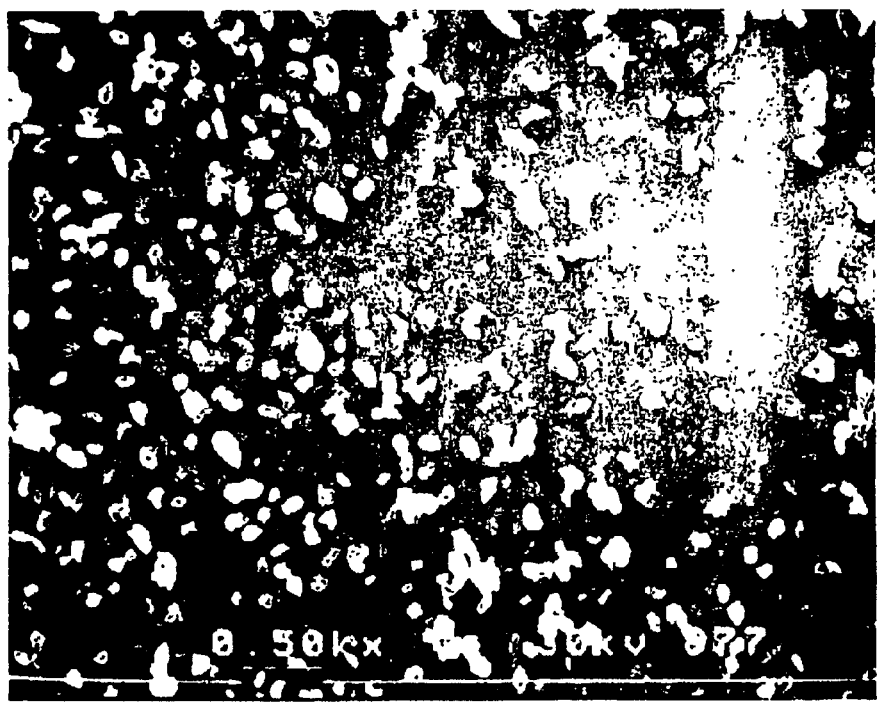
FIG. 8A–8C are SEM micrographs for 5% (A), 10% (B) and 20% (C) MSA.
Figure 8B:
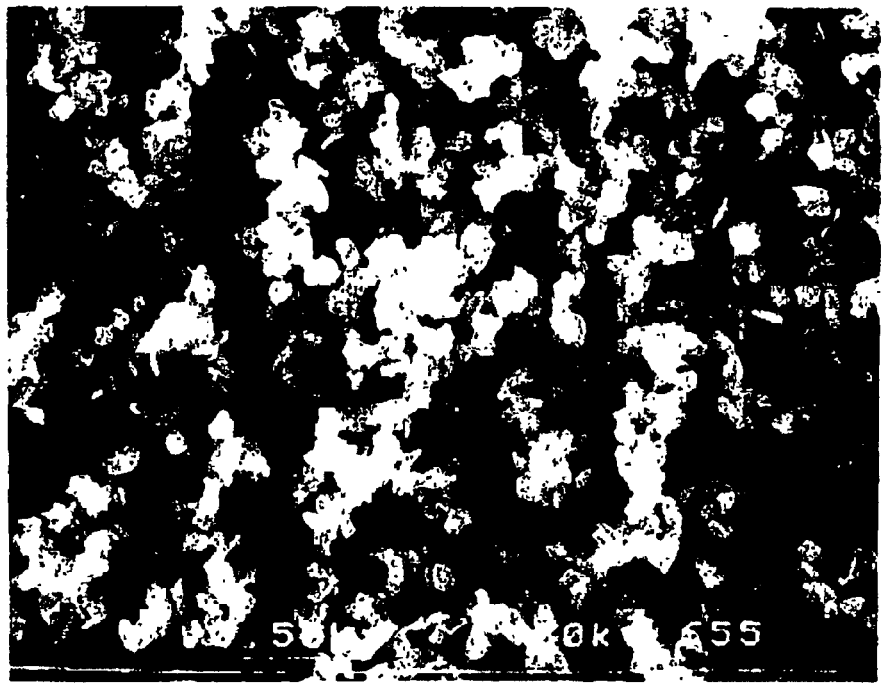
Figure 8C:
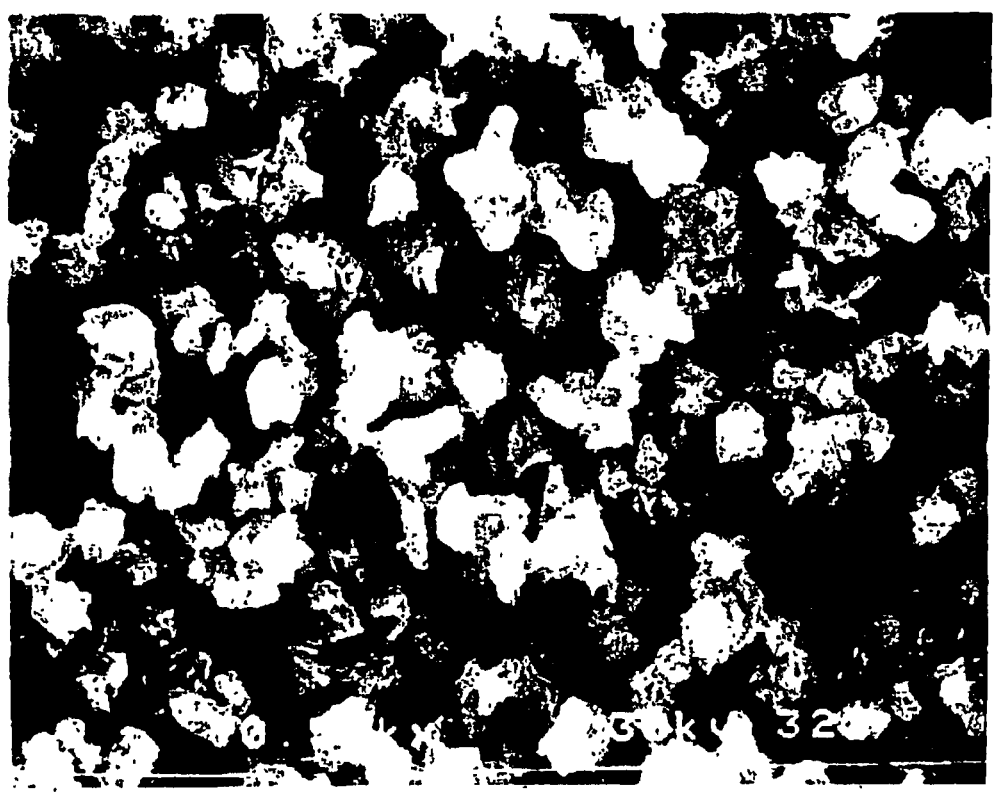

FIG. 8 shows SEM micrographs of PMSA particles prepared from 5% (FIG. 8A), 10% MSA (FIG. 8B) and 20% MSA (FIG. 8C). The experiment was performed at a temperature of 37° C. and a pressure of 85 bar. Notice the particle size increases with increasing concentration of MSA. The same magnification is used for all micrographs of FIG. 8 (500 times).

Triacylate Polymerization

Particles of triacrylate were also formed using the system as described above, using the following two compositions:

A: 10% 1,1,1-trimethylol propane triacrylate, 10% (by monomer weight) DMPA photoinitiator, 90% methylene chloride.

B. 15% triacrylate, 6% (by monomer weight) DMPA photoinitiator, 85% methylene chloride.

The experiments were carried out using carbon dioxide as the antisolvent, using a pressure of 85 bar and a temperature of 37° C.

Figure 9A:
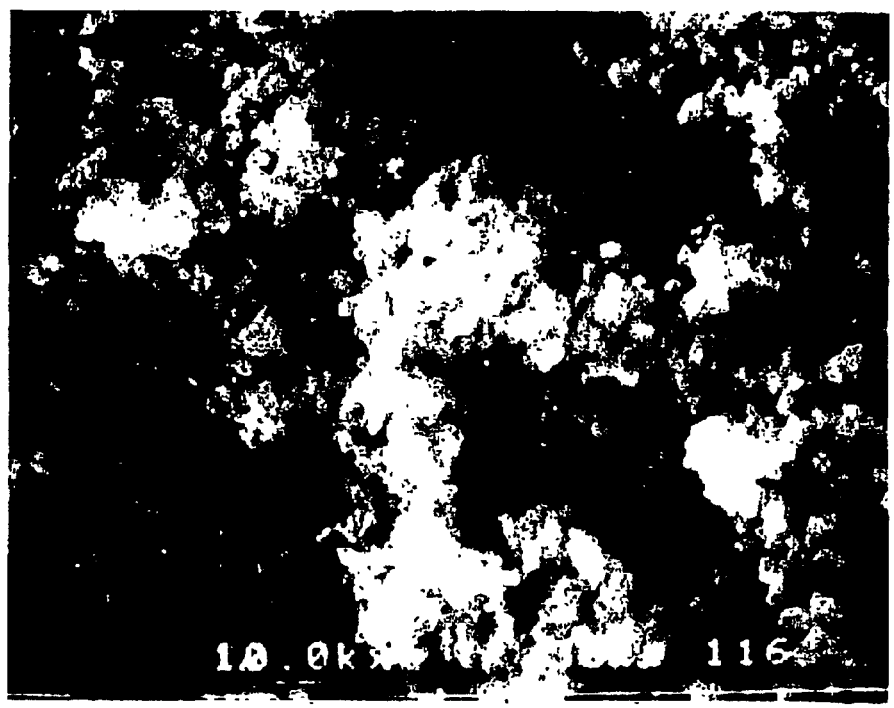
FIGS. 9A and 9B are SEM micrographs showing triacrylate polymers under two experimental conditions.
Figure 9B:
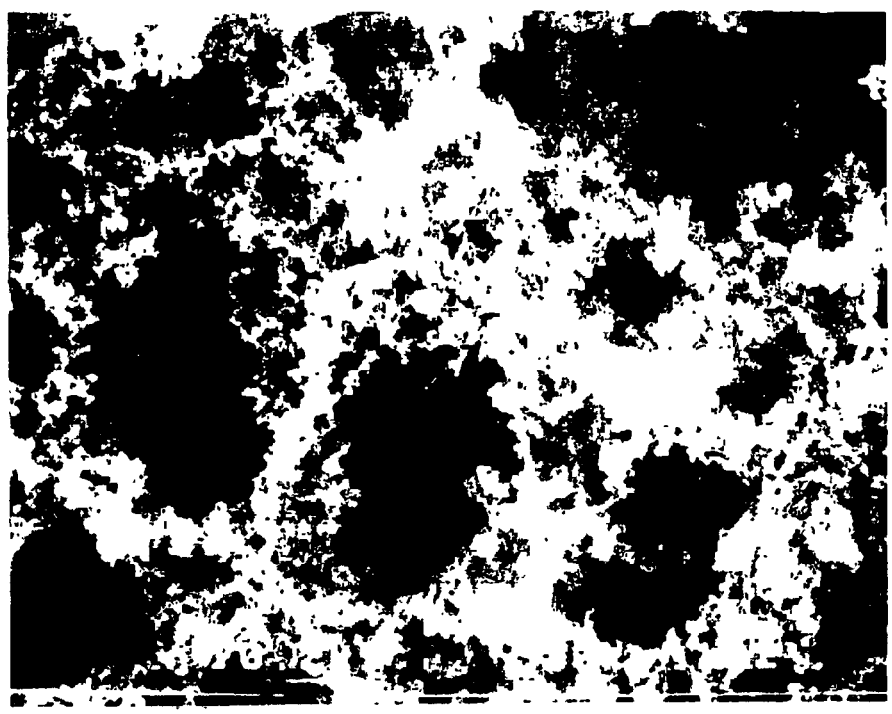

FIG. 9A shows a SEM micrograph of particles formed using condition A above at 10,000 times magnification. FIG. 9B shows a SEM micrograph of particles formed using condition B above at 10,200 times magnification.

Figure 10A:
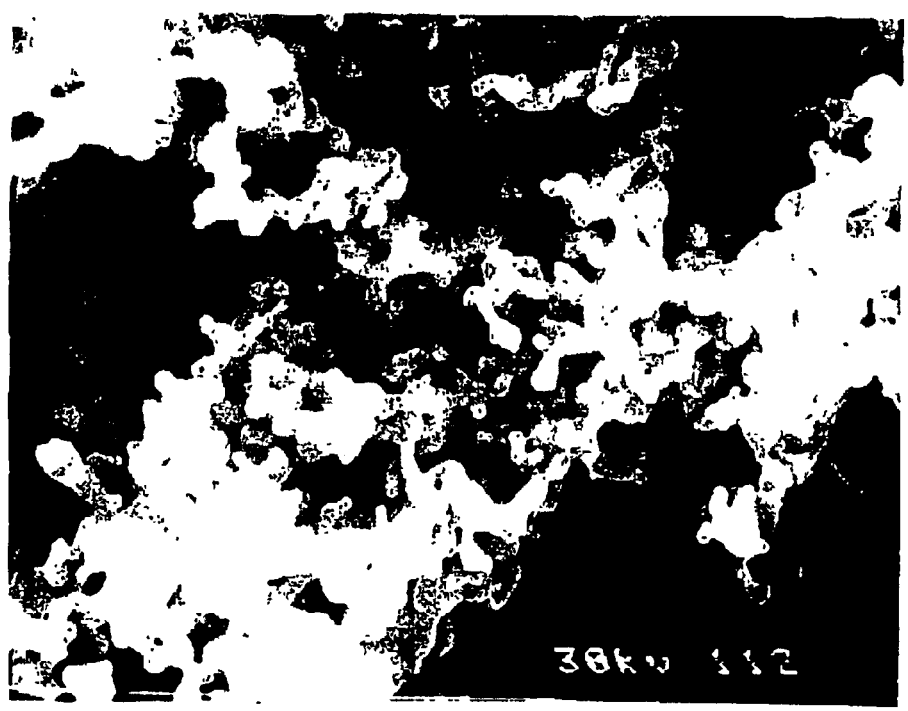
FIGS. 10A and 10B are SEM micrographs showing triacrylate polymers under two experimental conditions.
Figure 10B:
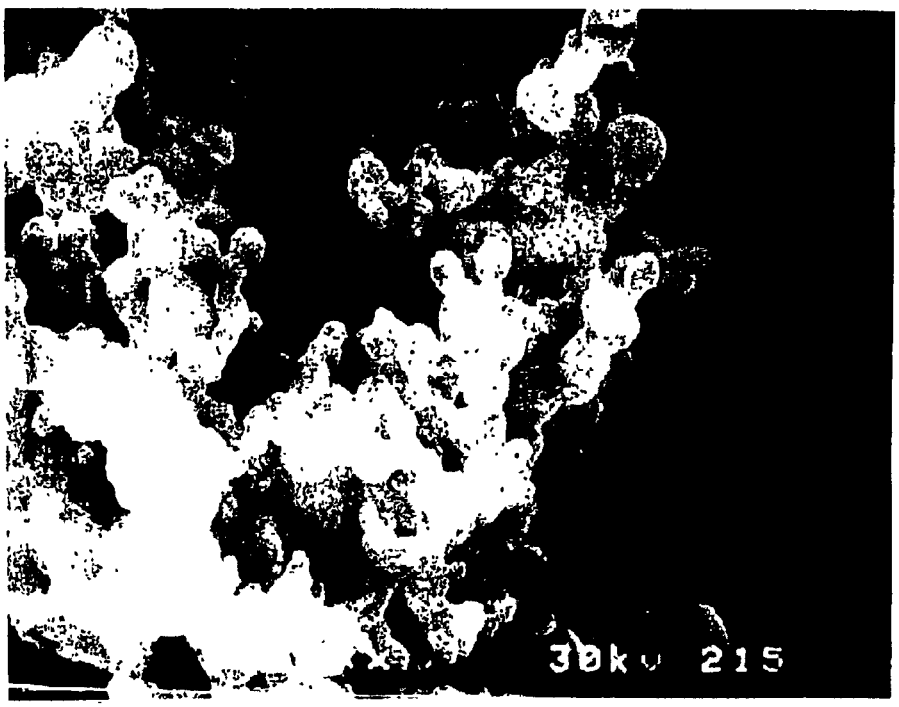

FIG. 10A shows a SEM micrograph of particles formed using condition A above at 5,200 times magnification. FIG. 10B shows a SEM micrograph of particles formed using condition B above at 5,100 times magnification.

Copolymer Formation

Copolymers of methacrylated sebacic anhydride (MSA) and polylactic acid (PLA) were formed using the methods of the invention using the following two compositions:

A: 2.5% MSA, 2.5% PLA, 95% methylene chloride, 20% (by monomer weight) DMPA photoinitiator.

B. 5% MSA, 5% PLA, 90% methylene chloride, 20% (by monomer weight) DMPA photoinitiator.

The experiments were carried out using carbon dioxide as the antisolvent, using a pressure of 85 bar and a temperature of 37° C.

Figure 11:
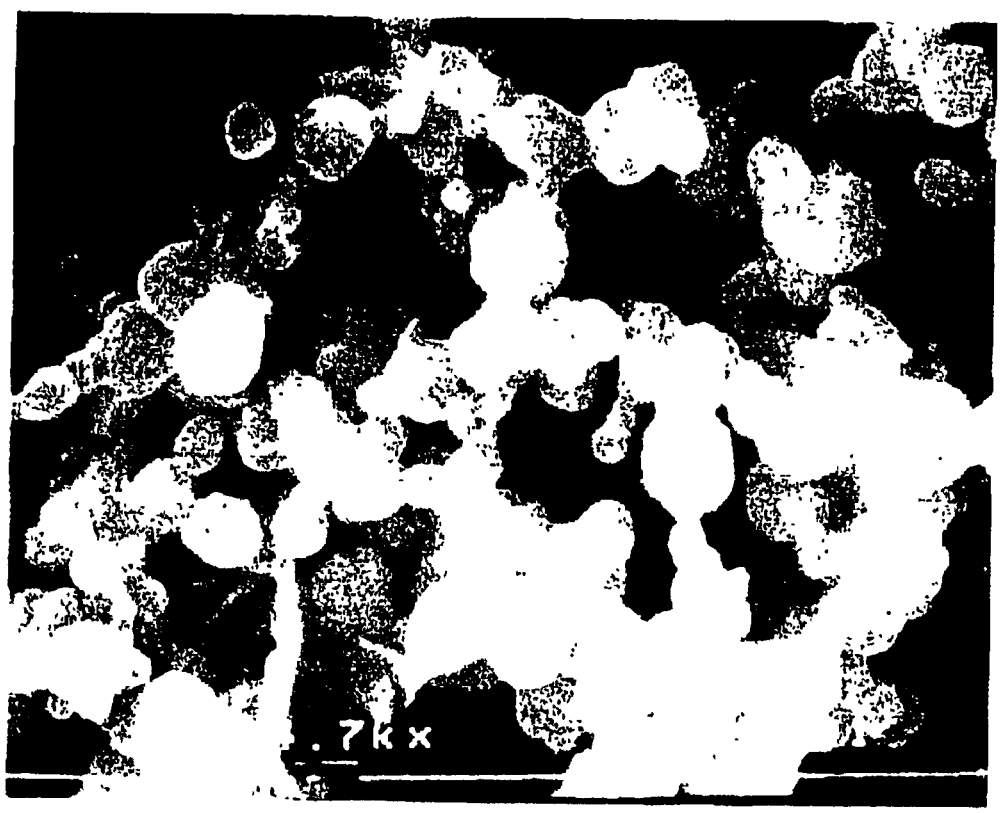
FIG. 11 is a SEM micrograph for 5% MSA/5% PLA copolymer.

The SEM of particles from system B are shown in FIG. 11 at 4700 times magnification.

Hydrophobic Ion Pairing

The drug tacrine, given to sufferers of Alzheimers disease, has been encapsulated homogeneously into these microparticles and the release behavior of the drug has been studied.

A 0.1 M aqueous solution of dodecyl sulfate, sodium salt (SDS) was prepared. In addition, a 5-mg/ml aqueous solution of Tacrine was also prepared.

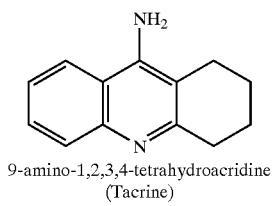

9-amino-1,2,3,4-tetrahydroacridine
(Tacrine)

Tacrine has one charged site available, and therefore requires a one to one pairing to a surfactant. The appropriate volumes of each solution were combined to obtain this stoichiometric ratio of SDS molecules to Tacrine molecules. The solution was then mixed vigorously for approximately 2 minutes. A cloudy solution results from the ion-paired precipitate and aqueous phases. Centrifuging the solutions for approximately 15 minutes at 6000 rpm separates the precipitate from the aqueous phase, allowing the aqueous phase to be removed easily. The wet precipitate was then dried under vacuum for 24 hrs before use in any further experimentation.

Figure 12:
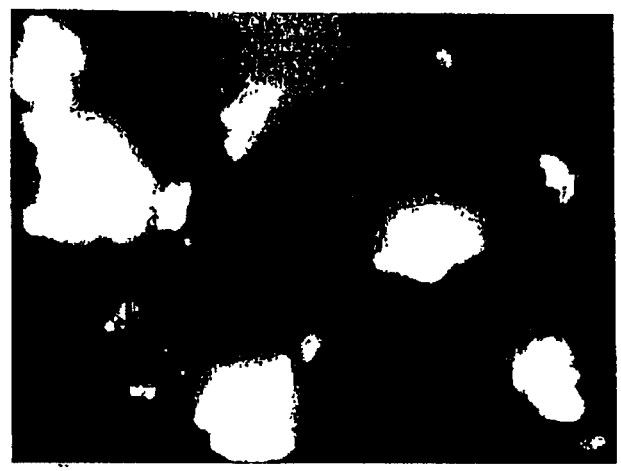
FIG. 12 is a fluorescence micrograph of PMSA particles encapsulated with tacrine.

Fluorescence imaging allowed the particles to be examined using a different technique since the Rose Bengal initiator is also a fluorescent material. FIG. 12 is a fluorescence microscopy image of PMSA microparticles encapsulated with tacrine magnified 20 times. Although not perfectly spherical, these particles exhibit a relatively round shape. From the fluorescence images of the particles, Rose Bengal appears to be evenly distributed on the particle surface. This image suggests that the Rose Bengal is dispersed throughout the particles, which may provide many initiation sites for a given particle. Many initiation sites could result in a non-uniform surface, where particle formation is dominated by nucleation and growth, rather than by atomization.

Drug Release Protocol

Approximately 2.5 mg of PMSA particles were placed into a 1.5 ml-capacity plastic centrifuge vial and filled with phosphate-buffered saline (PBS) (pH=7.4) at 37° C. The centrifuge tube was shaken to disperse the particles throughout the solution and placed in a 37° C. temperature bath for 3 minutes. The tube was then immediately centrifuged, and the buffer was drawn off and analyzed for drug concentration. The centrifuge tube was refilled with 37° C. PBS, and the cycle was repeated for about 3 hours. The tubes remained in the temperature bath for 3 minutes for the first hour, and 5–10 minutes for the remainder of the time data was collected. UV-Vis spectrophotometry (Model 8452, Hewlett Packard) was used to determine the concentration of tacrine (absorbance was measured at 322 nm) in experiment samples.

Figure 13:
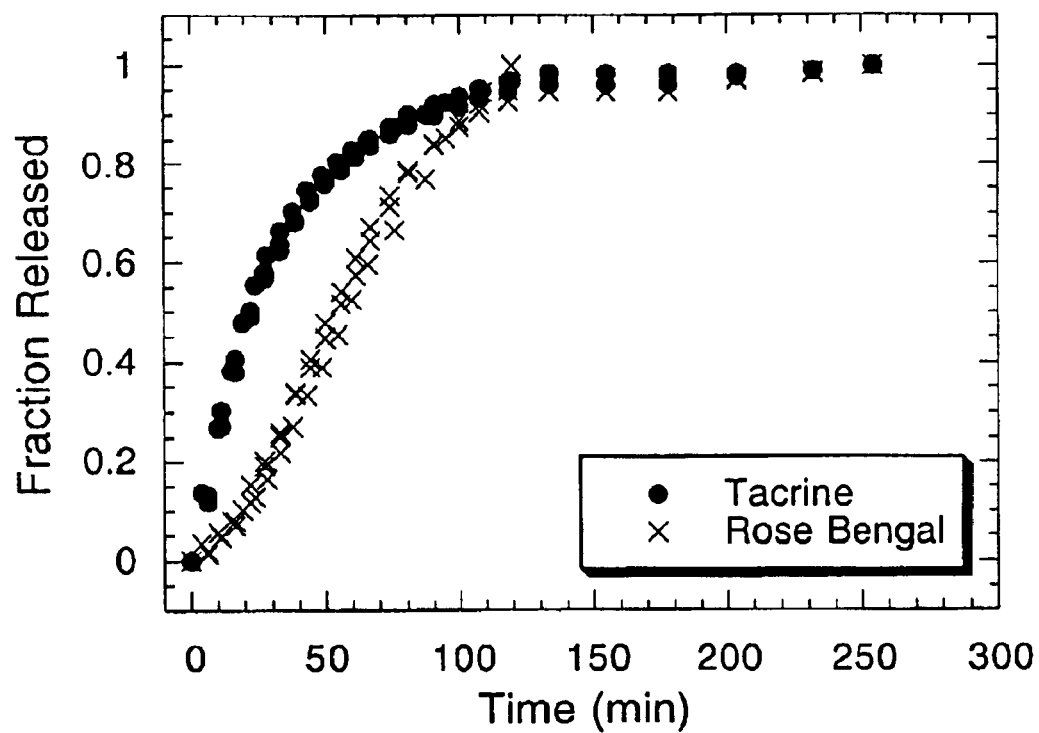
FIG. 13 shows release data from PMSA microparticles encapsulated with tacrine.

Drug release experiments illustrate the release properties of the microparticles formed in the photopolymerization PCA process. In all studies almost all of the particles degraded within 2 hours and this time scale is consistent with what can be calculated from the degradation kinetic constant of PMSA investigated by Muggli et al (Muggli, D. S. et al. (1999) J. Biomed. Mater. Res. 46:271–278). A 5–15 $\mu$n particle would degrade in about an hour, according to the calculated kinetic constant, but since oligomerized MSA was used, a longer degradation time should be expected. FIG. 13 shows the release profile of tacrine (absorbance measured at 322 nm (upper data)) and Rose Bengal (absorbance measured at 550 nm (lower data)) from the particles into PBS buffer. The tacrine release profile follows the curve for surface erosion of a sphere as expected. This profile concurs with SEM photographs that show that the particles have a round shape. The shape of the release profile of Rose Bengal indicates there is some influence of diffusion in the release. The Rose Bengal release profile is also affected by photobleaching of particles in room light. This may explain the lag time at the beginning of the Rose Bengal release in FIG. 13.

Release of Particles from an MSA Matrix

Crosslinked particles containing Rose Bengal were incorporated in a MSA matrix and polymerized into disks. Rose Bengal was also homogeneously incorporated into another set of MSA disks and polymerized. Advantages of using a particle-polymer composite include multi-mode degradation and release possible through the use of different biocompatible polymers and drugs, ease of control of surface degradation, and in one particular application, bone growth is facilitated by the resulting porous structures.

Disk samples were 0.25 to 0.3 grams, 13 mm diameter and 1.5 mm thick. Disks were placed in 10 ml of PBS buffer at 37° C. to monitor the degradation.

Figure 14:
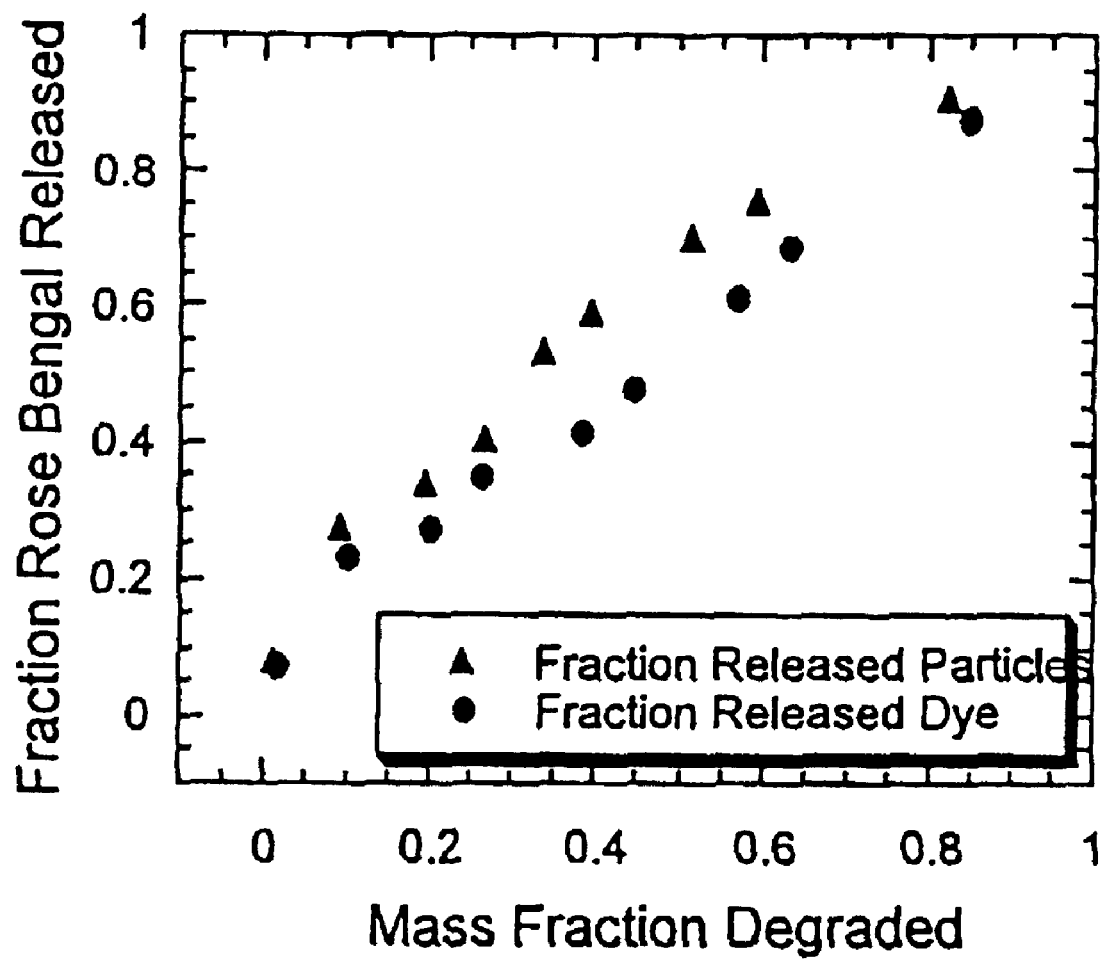
FIG. 14 shows release data from particles containing Rose Bengal incorporated in a MSA matrix and polymerized into disks and release data from Rose Bengal homogeneously incorporated into MSA disks and polymerized.

FIG. 14 shows release behavior for both sets of disks as a function of the mass fraction of the disks that had degraded. The absorbance of Rose Bengal was measured at 550 nm, and the disks were weighed to monitor the degradation. FIG. 14 shows a linear relationship between degradation and release for both homogeneous and heterogeneous disks.

One particular application of the particles is in bone cements. Particles release drugs over time as the bone cement (formed of degradable material) degrades and bone regrows.

Diacrylated Poly(ethylene glycol) (PEGDA) Polymerization

Particles of Poly(ethylene glycol) Diacrylate (PEGDA) were formed using the methods of the invention using the PEG1000DA monomer (PEG1kDA, Monomer-Poymer and Dajac Laboratories, Southhampton, Pa.). The experiments were carried out using methylene chloride as the solvent and carbon dioxide as the antisolvent, using a pressure of 85 bar and a temperature of 35° C. The photoinititator used was 2,2-dimethoxy-2-phenlyacetophenone (DMPA, Ciba Geigy, Tarrytown, N.Y.).

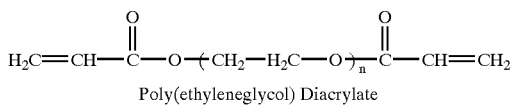

Poly(ethyleneglycol) Diacrylate

Figure 15:
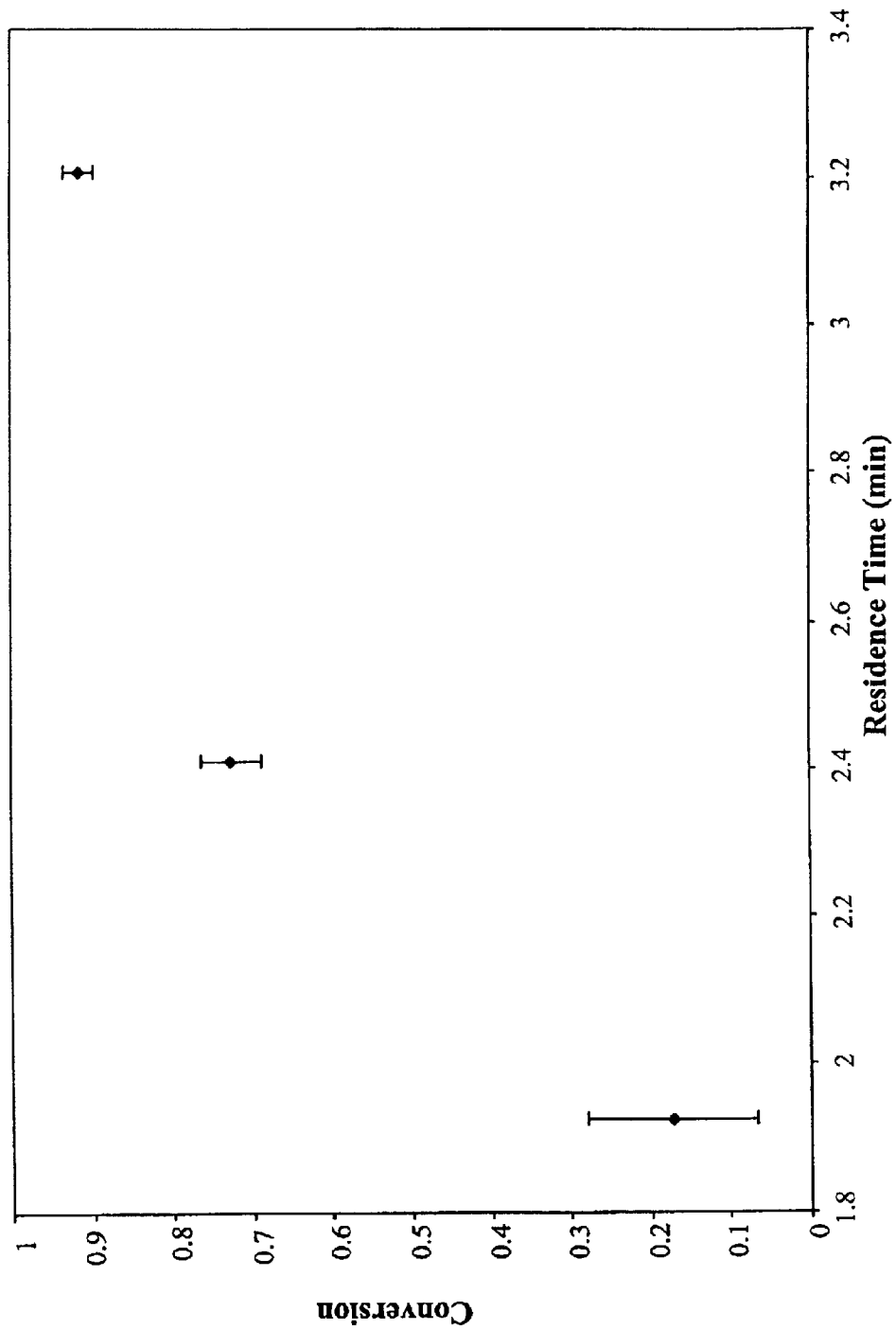
FIG. 15 shows the variation of double bond conversion with the residence time of the poly(ethylene glycol) diacrylate (PEGDA) particles in the apparatus.

FIG. 15 shows that the double bond conversion varied with the residence time of the particles in the apparatus. The solution used in these experiments had 25% PEG1000DA and 2% (by monomer weight) DMPA. The light intensity was 6 W/cm$^2$. The value of the double bond conversion indicates the extent of cross-linking. The particles corresponding to approx. 20% conversion were agglomerated. The residence time of the particles in the apparatus was varied by manipulating the combination of the antisolvent and solution flow rates.

The double bond conversion of the particles was determined through FTIR analysis compared to that of the PEG1000DA monomer. Particles were combined with mineral oil and crushed uniformly using a mortar and pestle to create a smooth paste of oil and crushed particles. A spectrum (64 scans averaged) was acquired in the mid-IR region of the resulting paste sandwiched between two KBR crystals. The same technique was used to make samples of the PEG1000DA monomer. Fractional conversion was calculated by subtracting the area of the carbon-carbon double bond peak of the reacted sample from that of the unreacted monomer and then dividing by the peak area of the unreacted monomer.

Figure 16A:
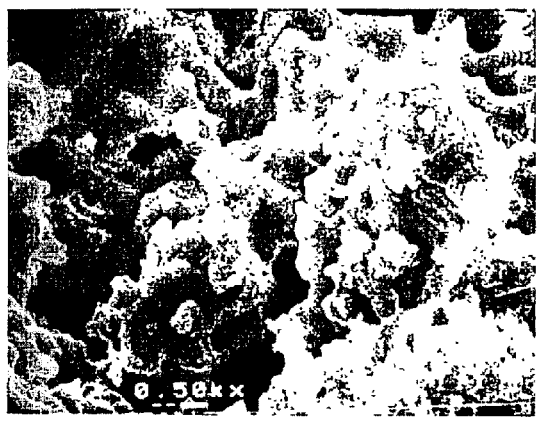
FIGS. 16A–D are SEM micrographs of PEGDA particles formed with photoinitiator concentrations of 1 (A), 1.5 (B), 2 (C), and 4 (D) percent by weight of the monomer.
Figure 16B:
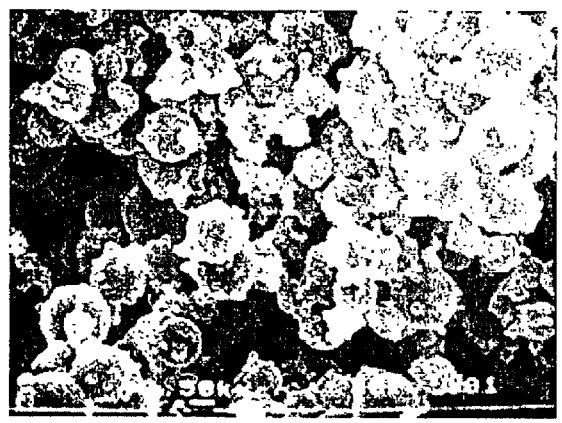
Figure 16C:
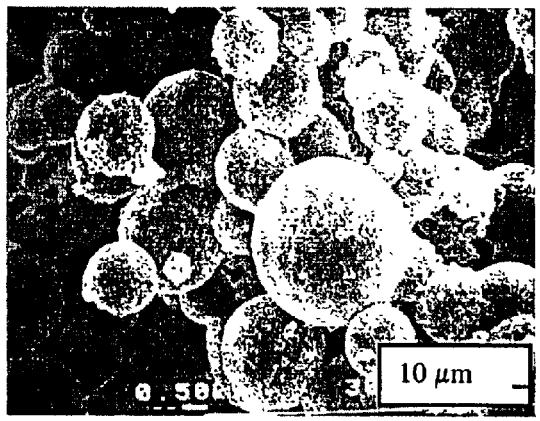
Figure 16D:
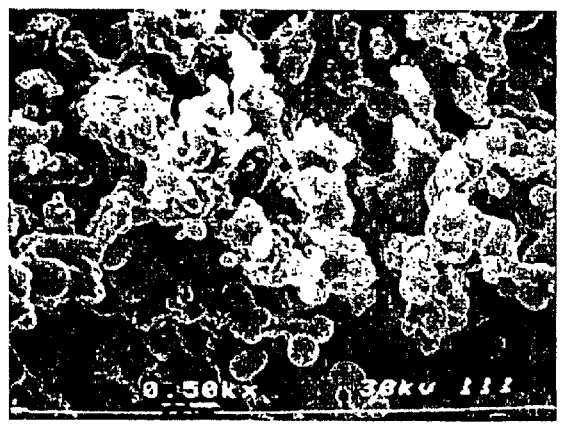

Experiments were also performed to assess the influence of the amount of photoinitiator on the process. FIGS. 16A–D, respectively, show SEM micrographs of the particles formed with photoinitiator concentrations of 1, 1.5, 2, and 4 percent by weight of the monomer (25 wt % monomer, 6W/cm$^2$ incident light intensity). The solution flow rate was 1 ml/min. As shown in FIGS. 16B and 16C, The 1.5 and 2 wt % initiator samples formed very smooth, spherical particles with diameters in the range 0.5 to 50 microns. In contrast, the samples processed with 1 and 4 wt % initiator generally look like agglomerated particles with little uniformity in structure, as is shown in FIGS. 16A and 16D. In the case of the 1 wt % DMPA photoinitiator sample, the rate of polymerization was likely insufficient to produce significant conversion that would prevent particle agglomeration. In the case of the 4 wt % DMPA photoinitiator sample, an excess of initiator likely led to decreased double bond conversion (Lovell, L. G.; Berchtold, K. A.; Elliott, J. E.; Lu, H.; Bowman, C. N. *Polym. Adv. Technol.* 2001, 12, 335–345. and Kloosterboer, *J. Adv. Poly. Sci.* 1988, 84, 1–61).

Figure 17A:
FIGS. 17A–C are SEM micrographs of PEGDA particles prepared with average incident light intensities of 3 (A), 4 (B), and 6.25 (C) W/cm$^2$.
Figure 17B:
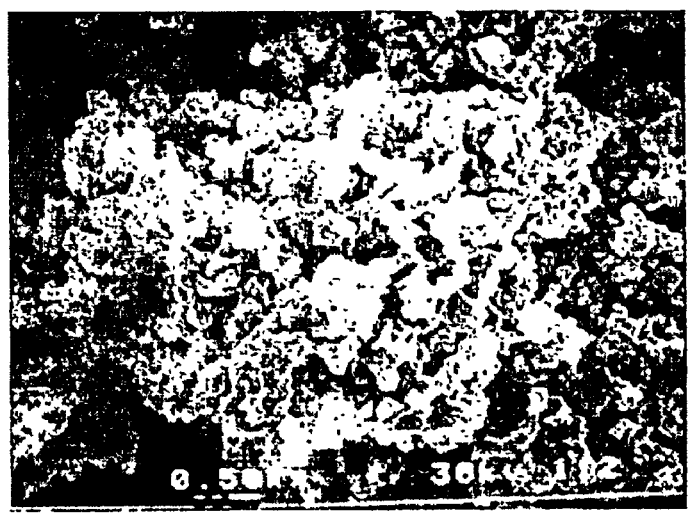
Figure 17C:
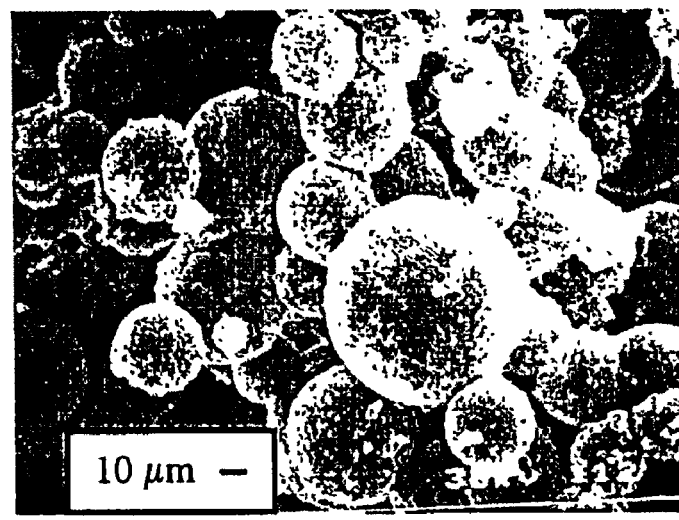

The effect of varying light intensity during the process was also examined. FIGS. 17A–C, respectively, show particles prepared with average incident light intensities of 3, 4, and 6.25 W/cm$^2$. The light intensities were measured using an EFOS Novacure Radiometer, Mississauga, Ontario, Canada. Other experimental conditions were 25 wt % monomer and 2 wt % photoinitiator relative to monomer. As shown in FIG. 17A, samples prepared at the low light intensity (3 W/cm$^2$) show little to no structure, judging from the large agglomerated masses and minimal evidence of particle formation. The medium intensity experiment (4 W/cm$^2$) exhibits an increased amount of particle formation but still significant numbers of aggregates (FIG. 17B). The high intensity experiment (6.25 W/cm$^2$) produced nicely formed spheres in size ranges from 1 to 50 microns (FIG. 17C). These results suggest that greater light intensity is more effective in producing crosslinked spherical particles in the limited time that the particles have to polymerize before they will interact with other particles in the high-pressure chamber due to fluid mixing that occurs in the process.

Calculation of Mesh Sizes for PEGDA Networks

The mesh sizes were calculated statistically assuming an ideal network and a monodisperse monomer molecular weight. For the starting macromer, PEG (—C—C—O—)$_n$, the PEG based chain had a bond length of 4.34 Angstroms for 2 C—O bonds at 1.4 angstroms each and one C—C bond at 1.54 Angstroms. For 100% double bond conversion, the length one side of the mesh was estimated as n*4.34 Angstroms. The length of the other side of the mesh was estimated to be the same as the kinetic chain length or C—C bond length. For an ideal network (100% conversion, no cyclization) the mesh size was estimated as the average of these 2 lengths.

For example, for 50% conversion, it was estimated that there will be a kinetic chain link every other monomer unit. The length of one side of the mesh was estimated as twice the sum of the bond lengths of the starting monomer multiplied by the number of monomer units. The length of the other side of the mesh can be estimated as the C—C bond length as before.

For a completely reacted system (100% double bond conversion) the calculated mesh sizes were 12.0 Angstroms for PEG200DA, 30 Angstroms for PEG 600DA, and 50.4 Angstroms for PEG1000DA. For a partially reacted system with 50% double bond conversion the calculated mesh sizes were 23.3 Angstroms for PEG200DA, 59.4 Angstroms for PEG 600DA, and 100.0 Angstroms for PEG1000DA.

Encapsulation Efficiencies

The encapsulation efficiency measured for tacrine in MSA was 92±4%, that in PEG1000DA was 31±7%, that for PEG600DA was 26±7%, and that for PEG200DA was 85±24%.

Although the description above contains many specificities, these should not be construed as limiting the scope of the invention but as merely providing illustrations of some of the presently preferred embodiments of the invention. For example, antisolvents other than carbon dioxide may be used. Other embodiments and uses are readily apparent to one of ordinary skill in the art without undue experimentation. Thus, the scope of the invention should be determined by the appended claims and their legal equivalents, rather than by the examples given. All references cited herein are hereby incorporated by reference to the extent not inconsistent with the disclosure herewith.

We claim:

1. A method for making crosslinked polymer particles with a desired double bond conversion amount comprising the steps of:
    exposing a composition comprising a polymer precursor, a non-aqueous solvent or solvent mixture, and an antisolvent or antisolvent mixture to photoradiation under conditions whereby crosslinked particles of the desired conversion amount are formed, wherein the antisolvent is a supercritical or near supercritical fluid in which the polymer precursor is not substantially soluble.

2. The method of claim 1, wherein the double bond conversion amount is between about 70% and 100%.

3. The method of claim 1, wherein the double bond conversion amount is between about 20% and about 100%.

4. The method of claim 1, wherein the polymer precursor has a carbon-carbon double bond functional group.

5. The method of claim 4, wherein the carbon-carbon double bond functional group is selected from the group consisting of acrylates and methacrylates.

6. The method of claim 1, further comprising the step of washing the particles with supercritical fluid, whereby the polymer particles comprise less than about 1% of residual solvent.

7. A method for making crosslinked polymer particles having a desired network mesh size comprising the steps of:
    selecting a polymer precursor;
    determining a double bond conversion amount which corresponds to the desired network mesh size for the polymer;
    exposing a composition comprising the polymer precursor, a non-aqueous solvent or solvent mixture, and an antisolvent or antisolvent mixture to photoradiation under conditions whereby crosslinked particles having the double bond conversion amount are formed, wherein the antisolvent is a supercritical or near supercritical fluid in which the polymer precursor is not substantially soluble and whereby the crosslinked particles have the desired network mesh size.

8. The method of claim 7 wherein the network mesh size is between about 10 and about 500 Angstroms.

9. The method of claim 7, wherein the polymer precursor has a carbon-carbon double bond functional group.

10. The method of claim 9, wherein the carbon-carbon double bond functional group is selected from the group consisting of acrylates and methacrylates.

11. The method of claim 7, further comprising the step of washing the particles with supercritical fluid, whereby the polymer particles comprise less than about 1% of residual solvent.

* * * * *